United States Patent [19]

Kaltenbronn et al.

[11] Patent Number: 5,126,451
[45] Date of Patent: Jun. 30, 1992

[54] RENIN INHIBITORS CONTAINING α-HETEROATOM AMINO ACIDS

[75] Inventors: James S. Kaltenbronn; Joseph T. Repine, both of Ann Arbor, Mich.

[73] Assignee: Warner-Lambert Company, Morris Plains, N.J.

[21] Appl. No.: 677,007

[22] Filed: Mar. 28, 1991

Related U.S. Application Data

[60] Division of Ser. No. 200,444, Jun. 6, 1988, Pat. No. 5,036,054, which is a continuation-in-part of Ser. No. 154,727, Feb. 11, 1988, abandoned.

[51] Int. Cl.⁵ .................. C07D 295/26; A61K 37/00
[52] U.S. Cl. .................................................. 544/159
[58] Field of Search ......................................... 544/159

[56] References Cited

FOREIGN PATENT DOCUMENTS 0094815 5/1983 European Pat. Off. .
0155809 3/1985 European Pat. Off. .

OTHER PUBLICATIONS

Tetrahedron, v. 31, pp. 863 to 866, U. Zoller et al., "Amidoalkylation of Mercaptans with Glyoxylic . . . ".
J. Org. Chem., 1986, 51, 3718–3720, M. G. Bock et al., "Differentially Protected α-Aminoglycine".

Primary Examiner—Mark L. Berch
Attorney, Agent, or Firm—Elizabeth M. Anderson

[57] ABSTRACT

The invention concerns novel renin-inhibitory peptides which contain novel amino acids having an α-heteroatom attached to the backbone of the amino acid.

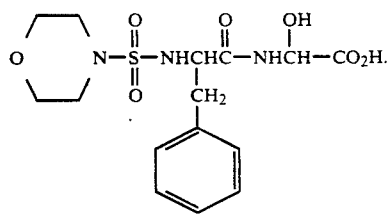

These novel amino acids are positioned at the $P_2$ position of the peptide. These are useful for treating renin-associated hypertension, hyperaldosteronism, and congestive heart failure. Processes for preparing the peptides, compositions containing them and methods of using them are included. Novel intermediates are also disclosed. Also included is a diagnostic method which uses the compounds to determine the presence of renin-associated hypertension or hyperaldosteronism.

1 Claim, No Drawings

RENIN INHIBITORS CONTAINING α-HETEROATOM AMINO ACIDS

This is a divisional application of U.S. Ser. No. 07/200,444 filed Jun. 6, 1988, now U.S. Pat. No. 5,036,054 which is a continuation-in-part application of U.S. Ser. No. 07/154,727 filed Feb. 11, 1988, now abandoned.

BACKGROUND OF THE INVENTION

Renin is a natural enzyme which is released into the blood from the kidney. It cleaves its natural substrate, angiotensinogen, releasing decapeptide, angiotensin I. This is in turn cleaved by converting enzyme in the lung, kidney and other tissues to an octapeptide, angiotensin II. Angiotensin II raises blood pressure both directly by causing arteriolar constriction and indirectly by stimulating release of the sodium-retaining hormone aldosterone from the adrenal gland causing a rise in extracellular fluid volume. Inhibitors of renin have been sought as agents for control of hypertension and hyperaldosteronism.

The present invention concerns a series of novel peptides which inhibit renin. It also concerns pharmaceutical compositions containing these novel peptides, methods of treating renin-associated hypertension, congestive heart failure, and hyperaldosteronism, as well as the use of the peptides as diagnostic tools, and the methods for preparing the peptides.

Structurally the compounds of the instant invention represent a new class of peptides, in that they contain an amino acid bearing an α-heteroatom directly attached to the amino acid backbone. The positions of the various amino acids may be designated by reference to the octapeptide which is the minimal angiotensinogen sequence cleaved by renin, namely:

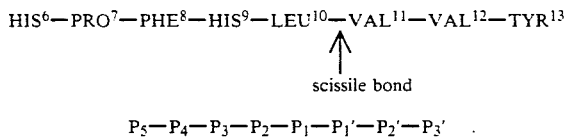

$$P_5\text{—}P_4\text{—}P_3\text{—}P_2\text{—}P_1\text{—}P_1'\text{—}P_2'\text{—}P_3'$$

A designation for the compounds of this invention is illustrated below. The STA is considered to occupy the $P_1$—$P_1'$ positions. For example

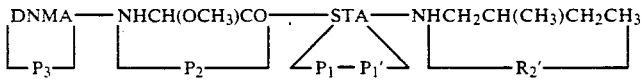

The compounds of this invention have the α-heteroatom amino acid at the $P_2$ position. It is surprising to find good activity in these compounds.

SUMMARY OF THE INVENTION

The present invention relates to novel peptides of the formula $$\text{ACYL—X—Y—W—U—V} \qquad (I)$$

and the pharmaceutically acceptable acid addition salts thereof wherein ACYL, X, Y, W, U, and V are as defined herein below.

The invention also includes pharmaceutical compositions comprising an effective amount of the above peptide of formula I in admixture with a pharmaceutically acceptable carrier or excipient and a method for treating renin-associated hypertension in a patient suffering therefrom comprising administering to said patient the above pharmaceutical composition in unit dosage form.

Further the invention includes a pharmaceutical composition comprising an effective amount of a peptide of formula I above in admixture with a pharmaceutically acceptable carrier or excipient, and a method for treating hyperaldosteronism in a patient suffering therefrom comprising administering to said patient the above pharmaceutical composition in unit dosage form.

The invention also includes a pharmaceutical composition comprising an effective amount of a peptide of formula I above in admixture with a pharmaceutically acceptable carrier or excipient, and a method for treating congestive heat failure in a patient suffering therefrom comprising administering to said patient the above pharmaceutical composition in unit dosage form.

The present invention also includes the use of peptides of formula I above as diagnostic tools for the identification of cases of hypertension due to renin excess.

The invention further includes methods for preparing peptides of formula I above.

DETAILED DESCRIPTION

The following table provides a dictionary of the terms used in the description of the invention.

TABLE I

| Abbreviated Designation | Amino Acid |
|---|---|
| LEU | L-Leucine |
| D-LEU | D-Leucine |
| STA | 4(S)-Amino-3(S)-hydroxy-6-methylheptanoic acid |
| PHSTA | 4(S)-Amino-3(S)-hydroxy-5-phenylpentanoic acid |
| CYSTA | 4(S)-Amino-3(S)-hydroxy-5-cyclohexanepentanoic acid |
| NORSTA | 3(S)-Amino-2(R)-hydroxy-5-methylhexanoic acid |
| ILE | L-Isoleucine |
| D-ILE | D-Isoleucine |
| N-MeLEU | N-Methylleucine |
| N-MeILE | N-Methylisoleucine |
| PHE | L-Phenylalanine |
| HOMOPHE | Homophenylalanine |
| PGY | 2(S)-Aminopentanoic acid |
| VAL | L-Valine |
| NAPHTHLALA | Naphthylalanine |
| CYCLOHEXYLALA | Cyclohexylalanine |
| TYR | L-Tyrosine |
| O-MeTYR | O-Methyltyrosine |
| TRP | L-Tryptophane |
| ASTA | 3(R,S),4(S)-Diamino-6-methylheptanoic acid |
| ACYS | 3(R,S),4(S)-Diamino-5-cyclohexanepentanoic acid |
| CHSTA | 4(S)-Amino-3(S)-hydroxy-4-cyclohexanebutanoic acid |
| DFSTA | 4(S)-Amino-3(S)-hydroxy-2,2-difluoro-6-methylheptanoic acid |
| DFKSTA | 4(S)-Amino-3-oxo-2,2-difluoro-6-methylheptanoic acid |
| DFCYS | 4(S)-Amino-3(S)-hydroxy- |

TABLE I-continued

| Abbreviated Designation | |
|---|---|
| DFKCYS | 2,2-difluoro-5-cyclohexanepentanoic acid 4(S)-Amino-3-oxo-2,2-difluoro-5-cyclohexanepentanoic acid |
| DFCHS | 4(S)-Amino-3(S)-hydroxy-2-2-difluoro-4-cyclohexanebutanoic acid |
| DFKCHS | 4(S)-Amino-3-oxo-2,2-difluoro-4-cyclohexanebutanoic acid |
| | Acyl Group |
| TOS | p-Toluenesulfonyl |
| PHT | Phthaloyl |
| Z | Benzyloxycarbonyl |
| BOC | Tert-butyloxycarbonyl |
| DNMA | Di-(1-naphthylmethyl)acetyl |
| BMA | 3-Amino-3-methylbutanoyl |
| Z-BMA | 3-(Benzyloxycarbonyl-amino)-3-methylbutanoyl |
| BBSP | 2-Benzyl-3-(t-butylsulfonyl)propionyl |
| IVA | Isovaleryl |
| NVA | n-Valeryl |
| | Amides With |
| —NHCH$_2$Ph | Benzylamine |
| —NHCH$_2$—(cyclohexyl) | Cyclohexylmethylamine |
| —NHCH$_2$—(C$_6$H$_4$)—CH$_2$NHZ (BOC) | m-Xylene-di-amine (Z or BOC) |
| —NHCH$_2$—(C$_6$H$_4$)—CH$_2$NH$_2$ | m-Xylene-di-amine |
| —NH$_2$ | Ammonia |
| —NH—(piperidine)N—CH$_2$Ph | 4-Amino-N-benzyl-piperidine |
| —NH—(piperidine)NH | 4-Aminopiperidine |
| —NH—CH$_2$—(2-pyridyl) | 2-Aminomethylpyridine |
| —NHCH$_2$CH(CH$_3$)CH$_2$CH$_3$ | 2-Methylbutylamine |
| —NH—CH(CH$_2$OH)—CH(CH$_3$)CH$_2$CH$_3$ | 1-Hydroxymethyl-2-methylbutylamine |
| —NHCH$_2$CH$_2$N(morpholine) | 4-(2-Aminoethyl)morpholine |

| Abbreviated Designation | |
|---|---|
| | Protecting Group |
| Z | Benzyloxycarbonyl |
| BOC | Tert-butyloxycarbonyl |
| | Esters With |
| —OCH$_3$ | Methanol |
| —OC$_2$H$_5$ | Ethanol |
| O-t-Bu | t-Butanol |
| O-i-Pr | Isopropanol |
| | Solvents and Reagents |
| DMF | N,N-Dimethylformamide |
| HOBT.H$_2$O | Hydroxybenzotriazole hydrate |
| DCC | N,N'-Dicyclohexylcarbodiimide |
| HOAc | Acetic acid |
| Et$_3$N | Triethylamine |
| THF | Tetrahydrofuran |
| EtOH | Ethanol |
| MeOH | Methanol |
| Et$_2$O | Diethylether |
| EtOAc | Ethyl acetate |

The peptides of the present invention are repeated by the formula $$ACYL-X-Y-W-U-V \qquad (I)$$

or a pharmaceutically acceptable acid additional salt thereof, wherein

ACYL is BOC, IVA, NVA, DNMA, Z, BMA, BBSP,

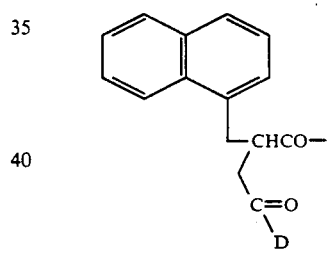

wherein D is

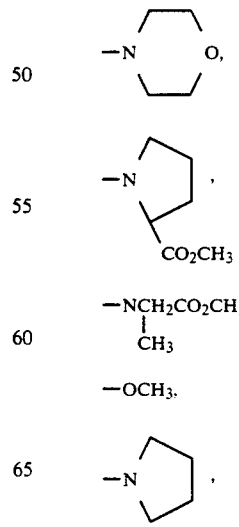

—N(morpholine)O,

—N(pyrrolidine with CO$_2$CH$_3$),

—NCH$_2$CO$_2$CH$_3$,
 |
 CH$_3$

—OCH$_3$,

—N(pyrrolidine),

-continued

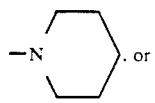

—N(CH₃)₂,

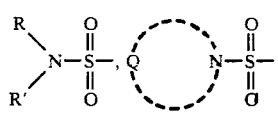

wherein R and R' are each independently hydrogen or straight or branched chain lower alkyl, Q̲ N̲ is a saturated ring containing 1 to 5 carbon atoms wherein Q is CH₂, O, S, or NR;

X is absent, PHE, HOMOPHE, NAPHTHYLALA, CYCLOHEXYLALA, O-MeTYR, TYR, or TRP, with the proviso that when ACYL is DNMA, BBSP, or

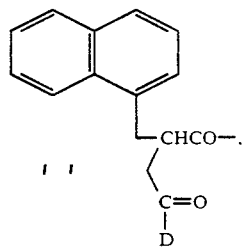

X is absent.
Y is

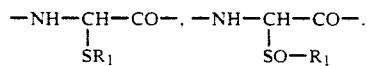

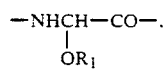

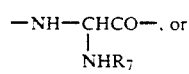

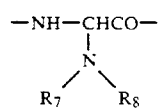

wherein R₁ is lower alkyl, lower alkenyl, lower alkynyl, aryl, heteroaryl, aralkyl,
(CH₂)ₙ—NHR₂, wherein n is an integer of from 2 to 4, and R₂ is

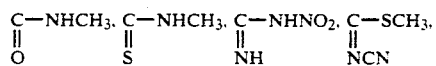

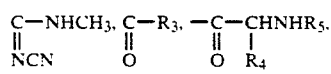

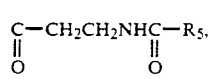

wherein R₃ is hydrogen, lower alkyl, or aryl, R₄ is H, lower alkyl or aralkyl, R₅ is

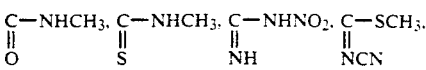

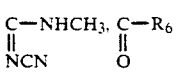

wherein R₆ is hydrogen, lower alkyl or aryl, wherein R₇ is R₁,

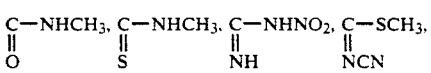

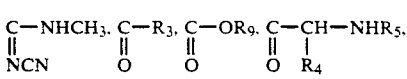

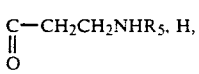

wherein R₈ is lower alkyl or together with R₇, when R₇ is lower alkyl, forms a heterocyclic ring containing from 4 to 6 carbon atoms optionally containing one or more S, O or NR; R₉ is alkyl or aralkyl;

W is STA, PHSTA, CYSTA, ASTA, ACYS, CHSTA, DFSTA, DFKSTA, DFCYS, DFKCYS, DFCHS, DFKCHS, or NORSTA;

U is absent, LEU, ILE, VAL, N-MeLEU, N-MeILE; and V is

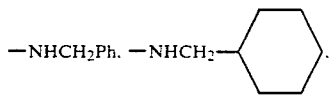

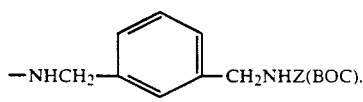

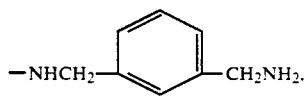

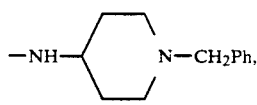

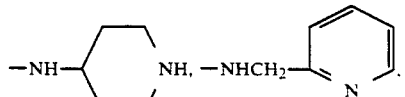

—NHCH₂CH(CH₃)CH₂CH₃, —OCH₃, —OC₂H₅,

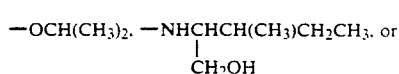

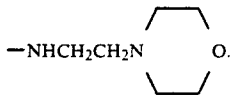

Preferred compounds of the present invention are those of formula I wherein in the Y fragment, the meaning of $R_1$ and $R_7$ are methyl, ethyl, isopropyl, propyl, allyl, propargyl, phenyl, benzyl,

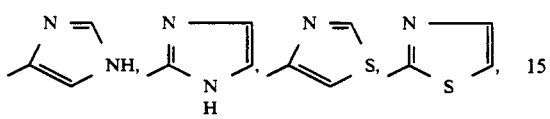

or $(CH_2)_n$—$CHR_2$, where n is an integer of from 2 to 4 and $R_2$ is

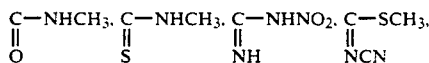

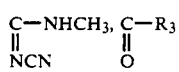

wherein $R_3$ is H or methyl,

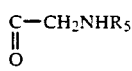

wherein $R_5$ is

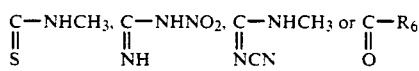

wherein $R_6$ is H or methyl.

Also preferred are compounds of formula I wherein $R_7$ is H

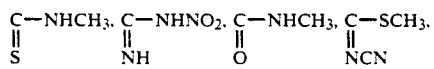

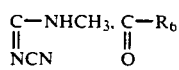

wherein $R_6$ is H or methyl

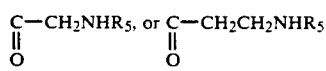

wherein $R_5$ is

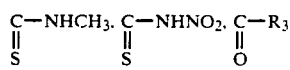

wherein $R_3$ is H or alkyl.

Also preferred are compounds according to claim 1 wherein in Y, $R_7$ and $R_8$ are each independently lower alkyl, or together form

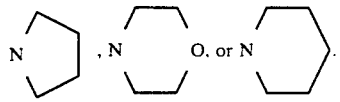

Other preferred compounds of the instant invention are represented by formula I wherein ACYL is BOC, IVA, DNMA, BMA, BBSP, or

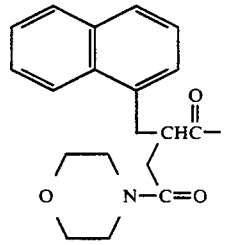

Other preferred compounds of the instant invention are those of formula I wherein W is STA, CYSTA, CHSTA, ACYS, DFKCYS, or DFKST.

Still other preferred compounds of the instant invention those of formula I wherein V is

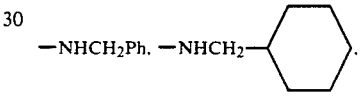

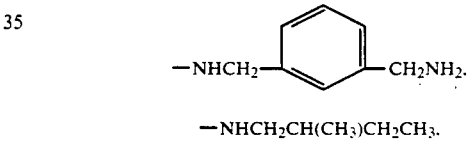

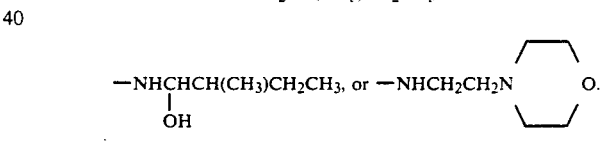

Particularly valuable compounds falling within the scope of the instant invention include the following:
DNMA—NHCH(OCH$_3$)CO—S-TA—NHCH$_2$CH9CH$_3$)CH$_2$CH$_3$,
DNMA—NHCH(SCH$_3$)CO—S-TA—NHCH$_2$CH9CH$_3$)CH$_2$CH$_3$,
DNMA—NHCH(SOCH$_3$)CO—S-TA—NHCH$_2$CH9CH$_3$)CH$_2$CH$_3$,
DNMA—NHCH(SCH(CH$_3$)$_2$)CO—S-TA—NHCH$_2$CH(CH$_3$)CH$_2$CH$_3$, (fast isomer),
DNMA—NHCH(SCH(CH$_3$)$_2$)CO—S-TA—NHCH$_2$CH(CH$_3$)CH$_2$CH$_3$, (flow isomer),
DNMA—NHCH(NH$_2$)CO—S-TA—NHCH$_2$CH(CH$_3$)CH$_2$CH$_3$ (fast isomer),
DNMA—NHCH(NH$_2$)CO—S-TA—NHCH$_2$CH(CH$_3$)CH$_2$CH$_3$ (slow isomer),
DNMA—NHCH(NHCO$_2$Et)CO—S-TA—NHCH$_2$CH(CH$_3$)CH$_2$CH$_3$,
DNMA—NHCH(OC$_2$H$_5$)CO—S-TA—NHCH$_2$CH(CH$_3$)CH$_2$CH$_3$ (fast isomer),
DNMA—NHCH(OC$_2$H$_5$)CO—S-TA—NHCH$_2$CH(CH$_3$)CH$_2$CH$_3$ (slow isomer), DNMA—NHCH(NH(CH₂)₃NHCSNHCH₃)CO—S-
TA—NHCH₂CH(CH₃)CH₂CH₃,
DNMA—NHCH(NHCOCH₃)CO—S-
TA—NHCH₂CH(CH₃)CH₂CH₃,
DNMA—NHCH(NHPh)CO—S-
TA—NHCH₂CH(CH₃)CH₂CH₃, DNMA—NHCH(N(CH₃)₂)CO—S-
TA—NHCH₂CH(CH₃)CH₂CH₃ (slow isomer),
DNMA—NHCH(NHCH(CH₃)₂)CO—S-
TA—NHCH₂CH(CH₃)CH₂CH₃ (slow isomer),
DNMA—NHCH(NHC₂H₅)CO—S-
TA—NHCH₂CH(CH₃)CH₂CH₃ (slow isomer,

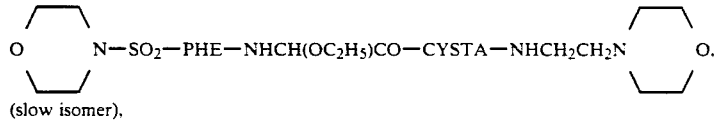
(slow isomer),

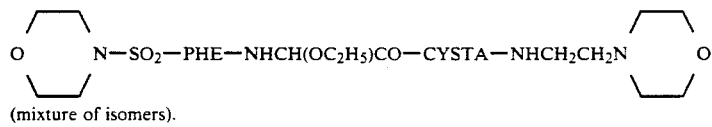
(mixture of isomers).

DNMA—NHCH(SPh)CO—S-
TA—NHCH₂CH(CH₃)CH₂CH₃.

Other valuable compounds falling within the scope of the invention are:

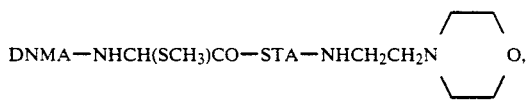

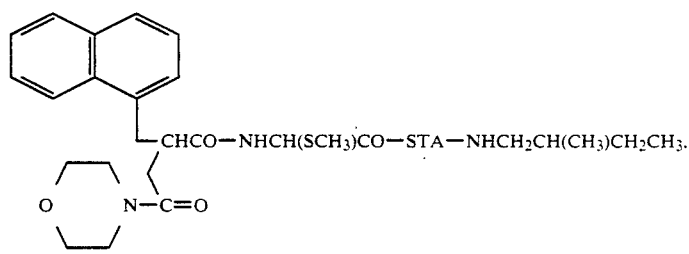

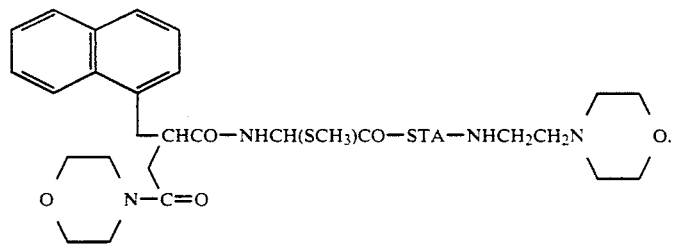

DNMA—NHCH(SCH₃)CO—CYSTA—NHCH₂CH(CH₃)CH₂CH₃,
DNMA—NHCH(SCH₃)CO—STA—LEU—NHCH₂Ph,

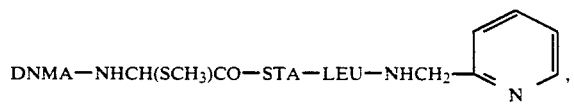

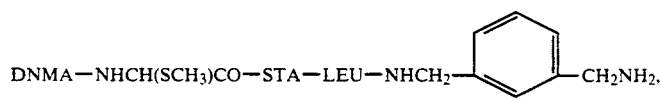

BOC—PHE—NHCH(SCH₃)CO—STA—NHCH₂CH(CH₃)CH₂CH₃.

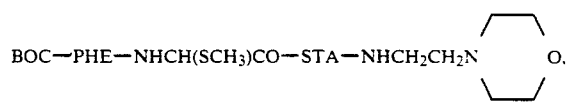

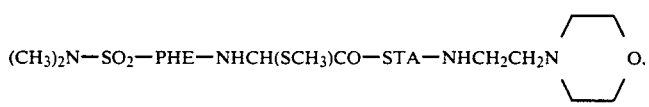
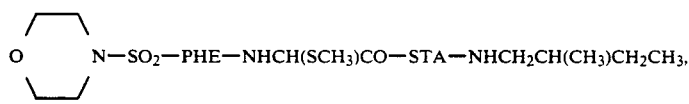
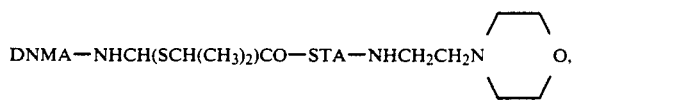
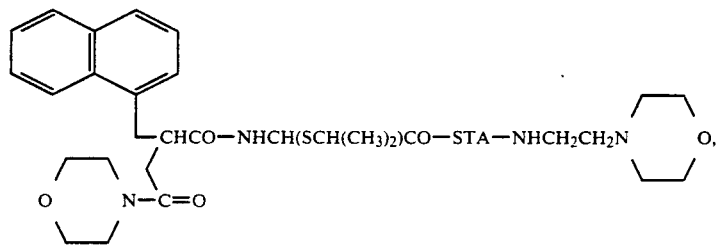
BOC—PHE—NHCH(SCH(CH₃)₂)CO—STA—NHCH₂CH(CH₃)CH₂CH₃.
(CH₃)₂N—SO₂—PHE—NHCH(SCH(CH₃)₂)CO—STA—NHCH₂CH(CH₃)CH₂CH₃.
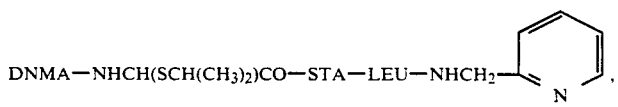
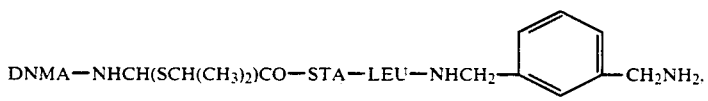
DNMA—NHCH(SPh)CO—STA—NHCH₂CH(CH₃)CH₂CH₃.
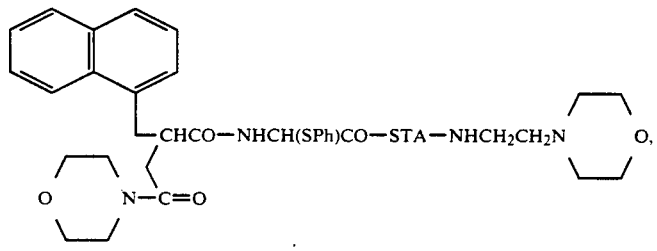
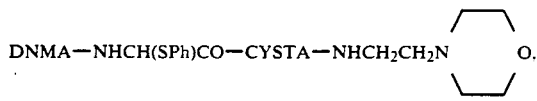
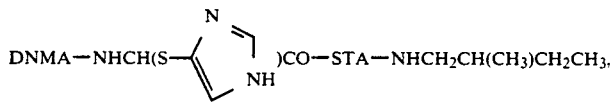
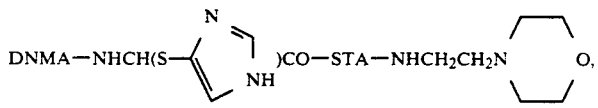

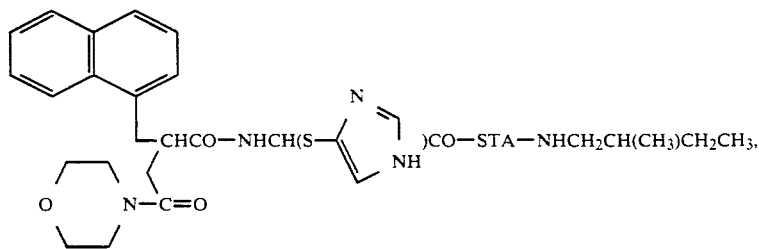
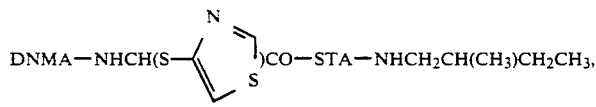
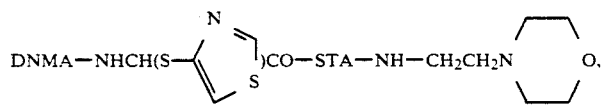
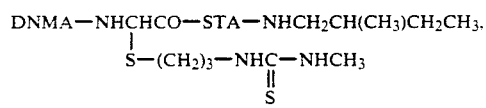
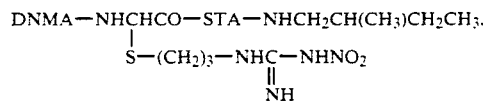
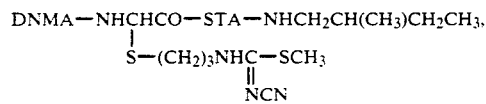
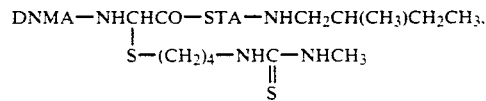
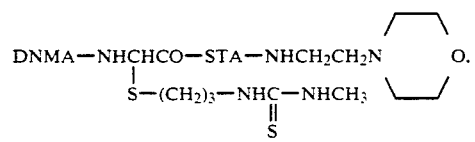
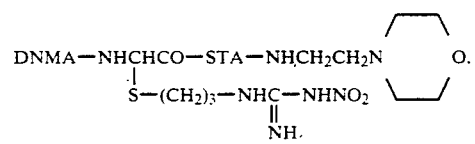
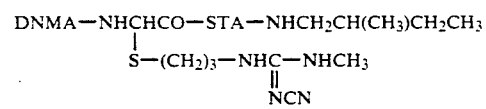
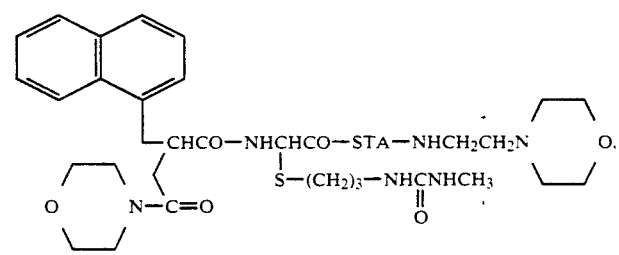

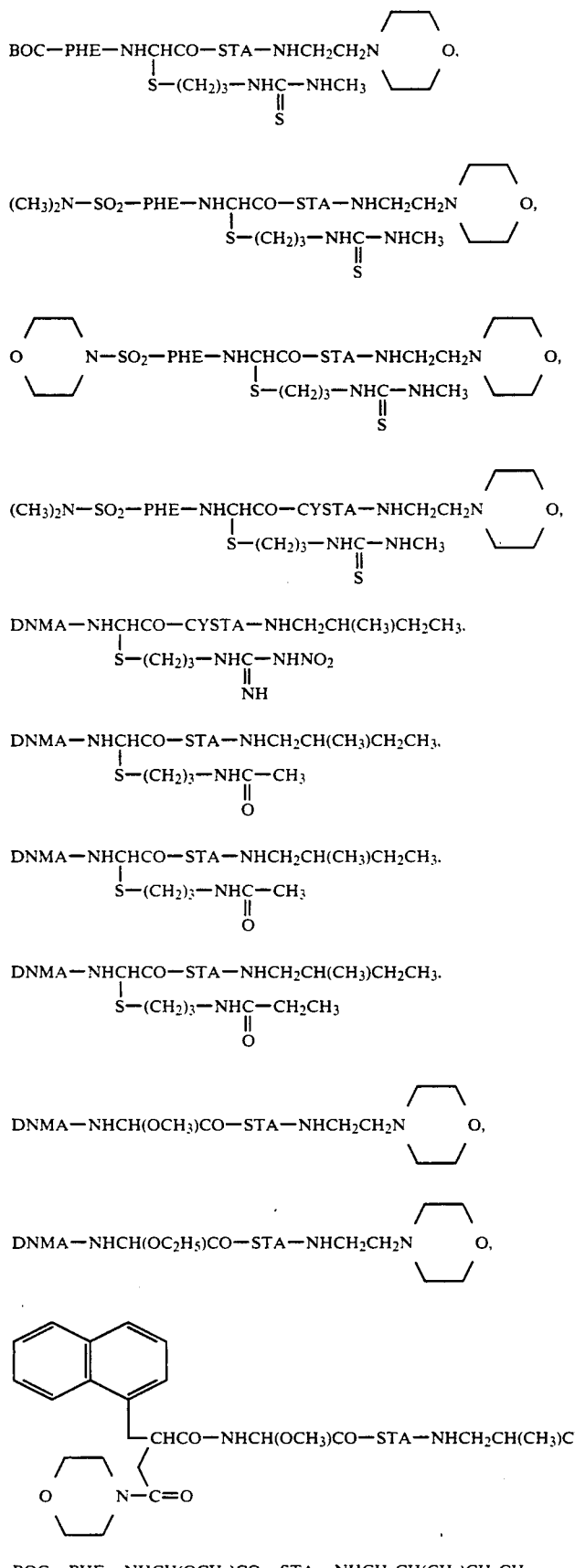

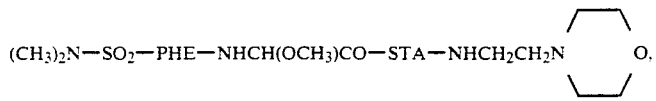(CH₃)₂N—SO₂—PHE—NHCH(OCH₃)CO—STA—NHCH₂CH₂N⟨morpholine⟩O,

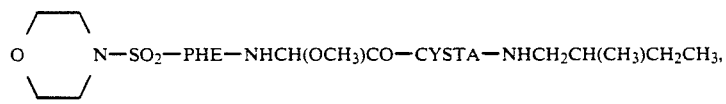O⟨morpholine⟩N—SO₂—PHE—NHCH(OCH₃)CO—CYSTA—NHCH₂CH(CH₃)CH₂CH₃,

DNMA—NHCH(OCH₃)CO—STA—LEU—NHCH₂Ph,

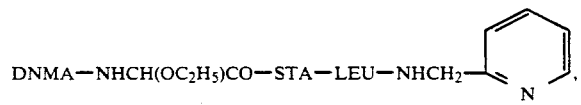DNMA—NHCH(OC₂H₅)CO—STA—LEU—NHCH₂-(2-pyridyl),

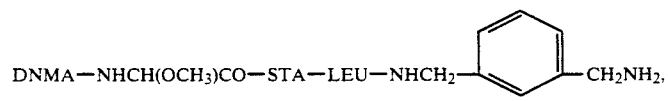DNMA—NHCH(OCH₃)CO—STA—LEU—NHCH₂-(C₆H₄)-CH₂NH₂,

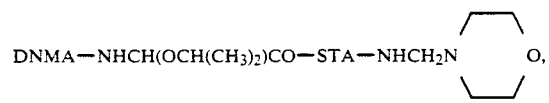DNMA—NHCH(OCH(CH₃)₂)CO—STA—NHCH₂N⟨morpholine⟩O,

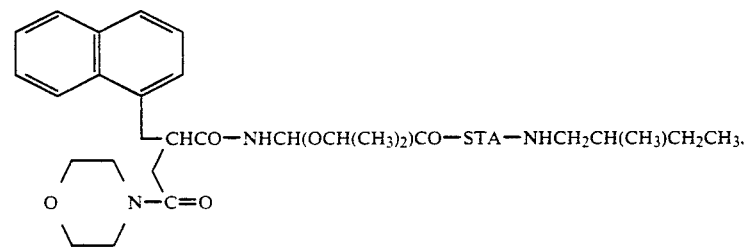
(1-naphthyl)CH₂-CH(CH₂-C(=O)-N⟨morpholine⟩)CO—NHCH(OCH(CH₃)₂)CO—STA—NHCH₂CH(CH₃)CH₂CH₃, DNMA—NHCH(OC₂H₅)CO—CYSTA—NHCH₂CH(CH₃)CH₂CH₃,
DNMA—NHCH(OPh)CO—STA—NHCH₂CH(CH₃)CH₂CH₃,

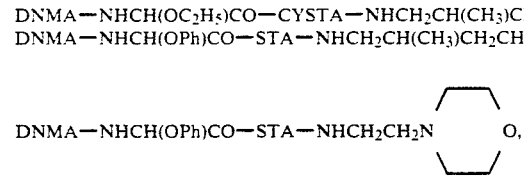DNMA—NHCH(OPh)CO—STA—NHCH₂CH₂N⟨morpholine⟩O,

BOC—PHE—NHCH(OPh)CO—STA—NHCH₂CH(CH₃)CH₂CH₃,

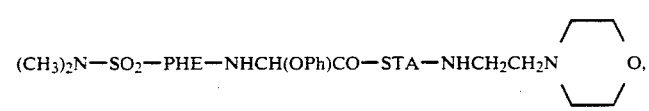(CH₃)₂N—SO₂—PHE—NHCH(OPh)CO—STA—NHCH₂CH₂N⟨morpholine⟩O,

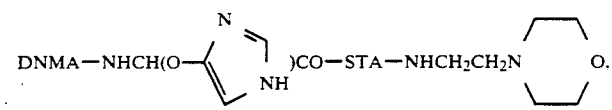DNMA—NHCH(O-(imidazolyl))CO—STA—NHCH₂CH₂N⟨morpholine⟩O.

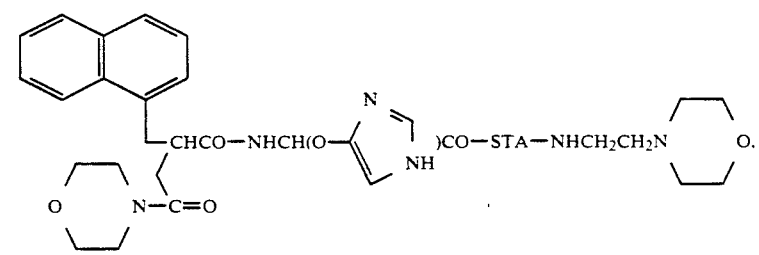
(1-naphthyl)CH₂-CH(CH₂-C(=O)-N⟨morpholine⟩)CO—NHCH(O-(imidazolyl))CO—STA—NHCH₂CH₂N⟨morpholine⟩O.

-continued
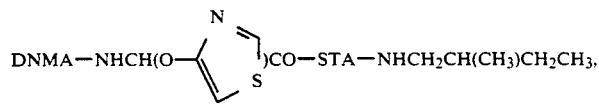
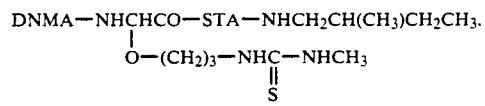
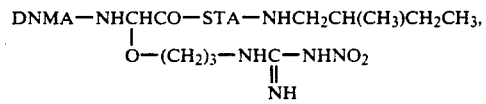
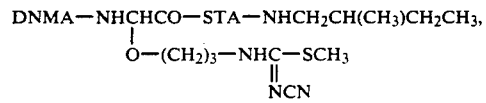
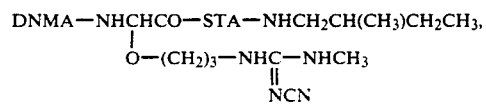
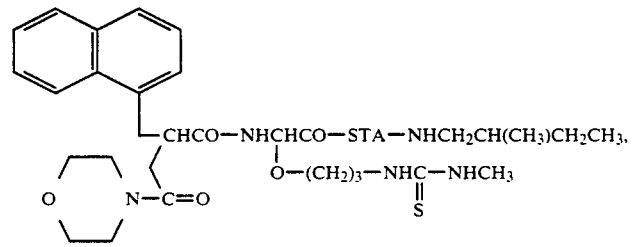
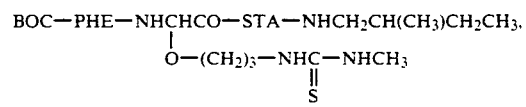
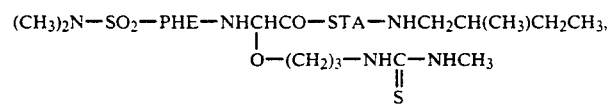
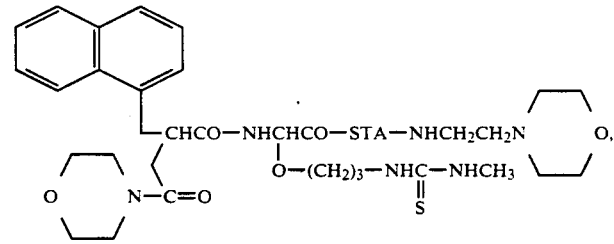
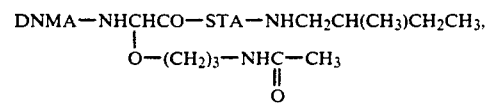
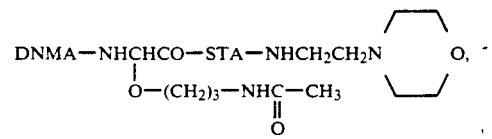
DNMA—NHCH(NHCH₃)CO—STA—NHCH₂CH(CH₃)CH₂CH₃,
DNMA—NHCH(N(CH₃)₂)CO—STA—NHCH₂CH(CH₃)CH₂CH₃.

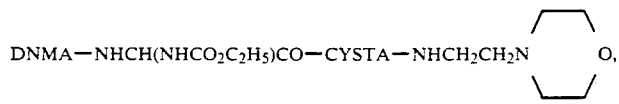
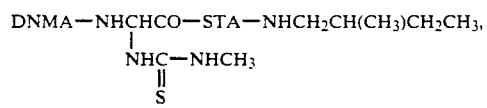
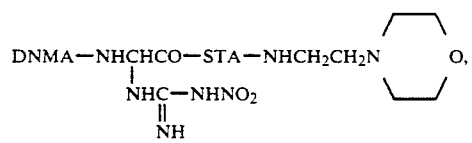
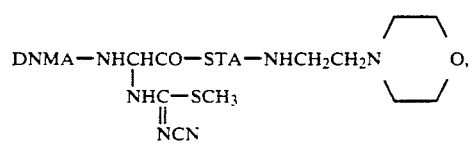
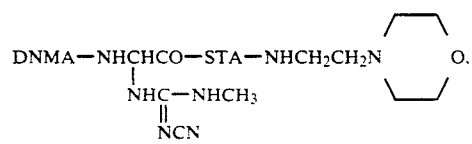
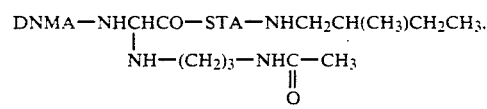
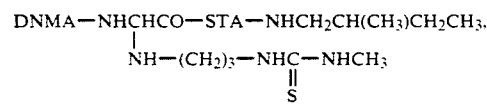
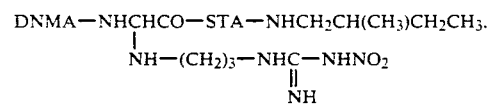
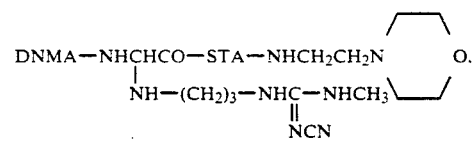
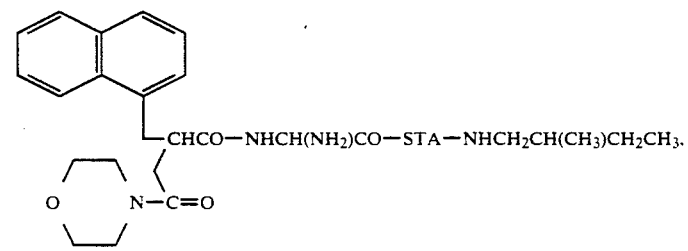
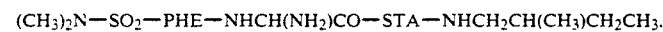
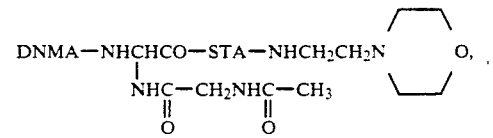

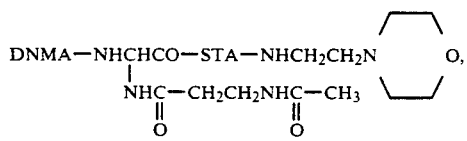
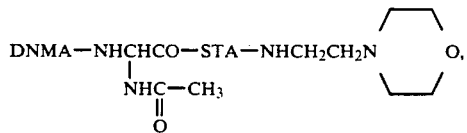
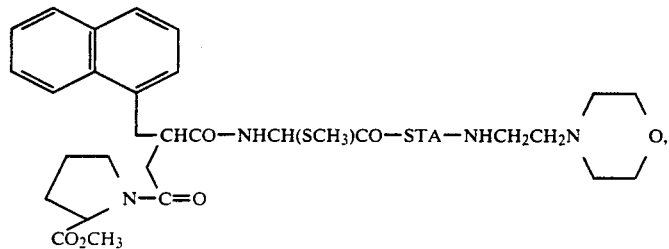
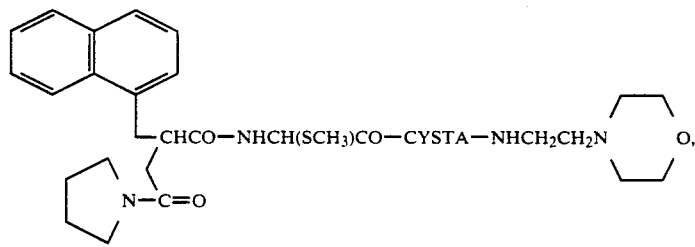
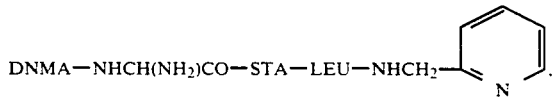
DNMA—NHCH(NH₂)CO—STA—LEU—NHCH₂Ph,
DNMA—NHCH(OCH₃)CO—NORSTA—O—CH(CH₃)₂,
DNMA—NHCH(SCH₃)CO—NORSTA—O—CH(CH₃)₂.
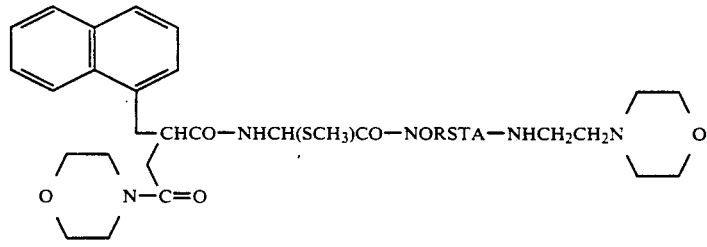
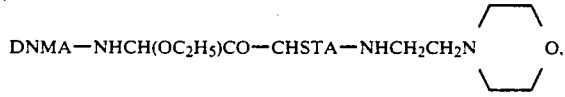
BBSP—NHCH(OC₂H₅)CO—DFKSTA—NHCH₂CH(CH₃)CH₂CH₃.
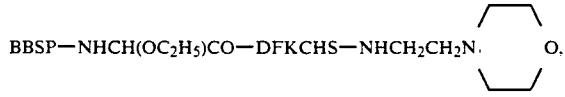

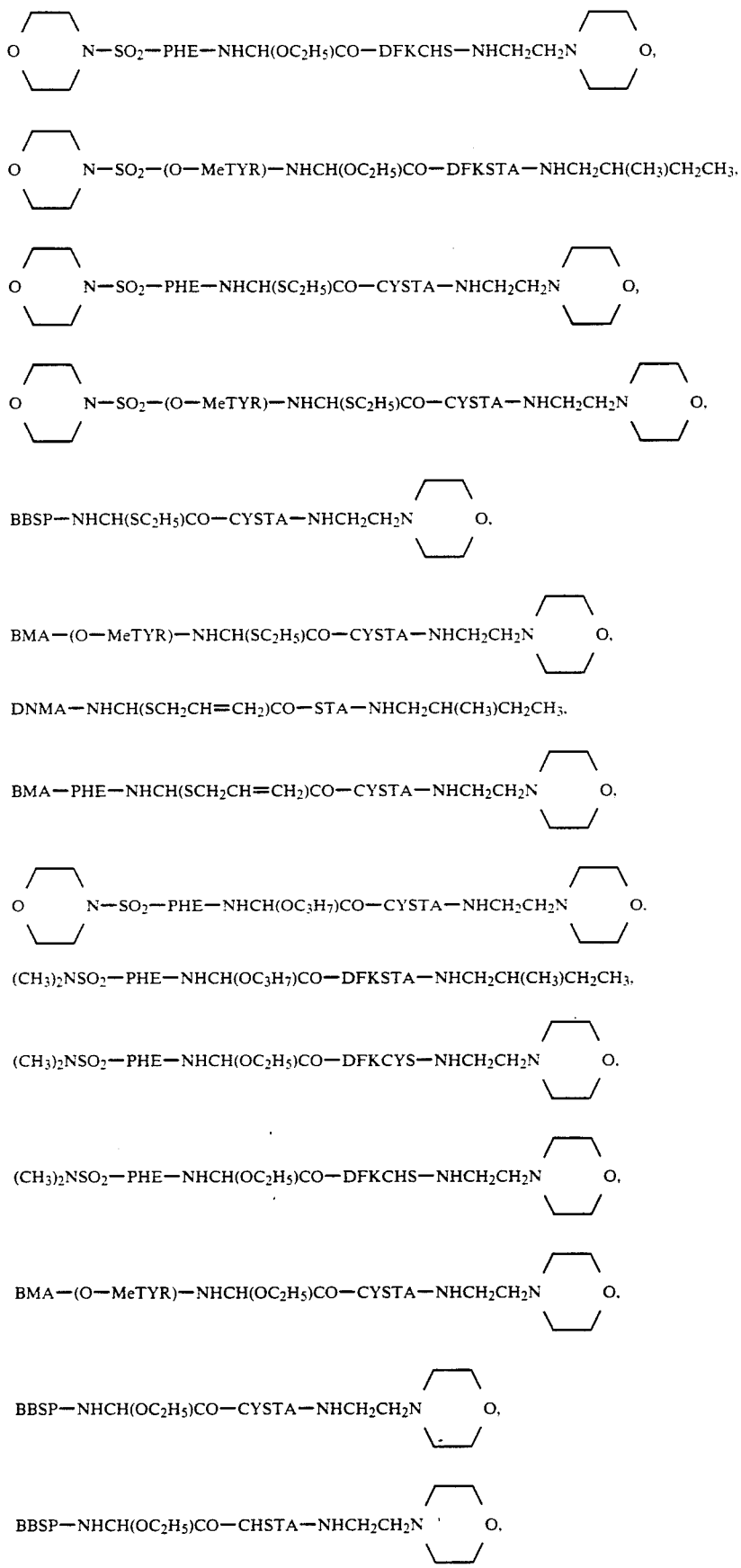

-continued

BBSP—NHCH(OC₂H₅)CO—ACYS—NHCH₂CH₂N⟨morpholino⟩O,

BBSP—NHCH(OC₂H₅)CO—ASTA—NHCH₂CH(CH₃)CH₂CH₃,

O⟨morpholino⟩N—SO₂—PHE—NHCH(OC₂H₅)CO—DFCYS—NHCH₂CH₂N⟨morpholino⟩O,

O⟨morpholino⟩N—SO₂—PHE—NHCH(OC₂H₅)CO—DFKCYS—NHCH₂CH₂N⟨morpholino⟩O,

O⟨morpholino⟩N—SO₂—PHE—NHCH(OC₂H₅)CO—ACYS—NHCH₂CH(CH₃)CH₂CH₃,

O⟨morpholino⟩N—SO₂—(O—MeTYR)—NHCH(OC₂H₅)CO—CYSTA—NHCH₂CH₂N⟨morpholino⟩O,

DNMA—NHCH(OCH₂CH=CH₂)CO—CYSTA—NHCH₂CH₂N⟨morpholino⟩O,

DNMA—NHCH(OCH₂C≡CH)CO—STA—NHCH₂CH(CH₃)CH₂CH₃.

BBSP—NHCH(OCH₂CH=CH₂)CYSTA—NHCH₂CH₂N⟨morpholino⟩O,

BMA—(O—MeTYR)—NHCH(OCH₂CH=CH₂)—STA—NHCH₂CH(CH₃)CH₂CH₃.
BMA—PHE—NHCH(OCH₂CH=CH₂)—DFKSTA—NHCH₂CH(CH₃)CH₂CH₃,

BBSP—NHCH(SCH₂C≡CH)CO—CYSTA—NHCH₂CH₂N⟨morpholino⟩O.

BMA—NHCH(SCH₂C≡CH)CO—CYSTA—NHCH₂CH₂N⟨morpholino⟩O.

BBSP—NHCH(S—⟨thiazole⟩)CO—CYSTA—NHCH₂CH₂N⟨morpholino⟩O,

BMA—NHCH(S—⟨thiazole⟩)CO—CYSTA—NHCH₂CH₂N⟨morpholino⟩O,

O⟨morpholino⟩N—SO₂—PHE—NHCH(S—⟨imidazole⟩)CO—CYSTA—NHCH₂CH₂N⟨morpholino⟩O,

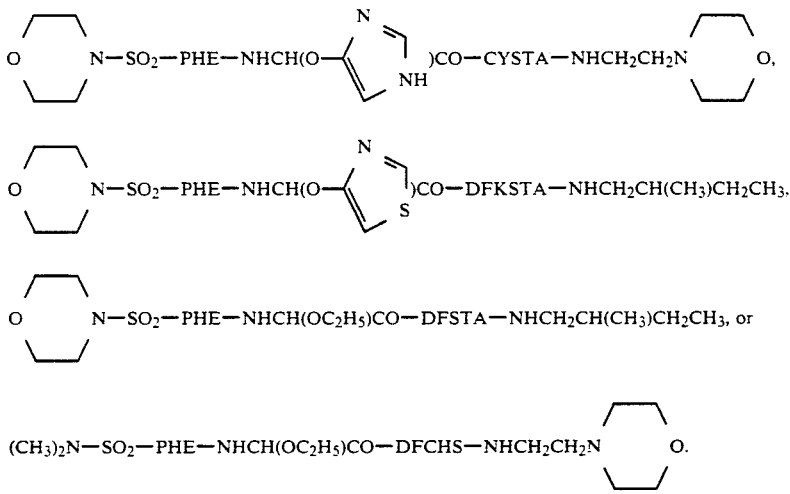

The compounds include solvents and hydrates and pharmaceutically acceptable acid addition salts of the basic compounds of formula I above.

The term pharmaceutically acceptable acid addition salt is intended to mean a relatively nontoxic acid addition salt either from inorganic or organic acids such as, for example, hydrochloric, hydrobromic, hydroiodic, sulfuric, phosphoric, acetic, citric, oxalic, malonic, salicylic, malic, benzoic, gluconic, fumaric, succinic, ascorbic, maleic, tartaric, methanesulfonic and the like. The salts are prepared by contacting the free base form with a sufficient amount of the desired acid to produce a salt in the conventional manner. The free base forms may be regenerated by treating the salt form with a base.

The modified peptides of the present invention possess one or more chiral centers and each center may exist in the R(D) or S(L) configuration. The present invention includes all enantiomeric and epimeric forms as well as the appropriate mixtures thereof.

Novel intermediates of the present invention include the following compounds:
DNMA—NHCH(OCH₃)CO₂CH₃,
DNMA—NHCH(OCH₃)CO₂H,
DNMA—NHCH(SCH₃)CO₂H,
DNMA—NHCH(SCH(CH₃)₂)CO₂H,
DNMA—NHCH(OH)CO₂H,
DNMA—NHCH(OC₂H₅)CO₂C₂H₅,
DNMA—NHCH(OC₂H₅)CO₂H,

Some of the above novel peptides may be prepared in accordance with well-known procedures for preparing peptides from their constituent amino acids. Other of the novel peptides of the present invention are prepared by a step-wise procedure or by a fragment coupling procedure depending upon the particular final product desired.

The following schemes illustrate novel methods of preparing certain peptides of the present invention.

SCHEME I

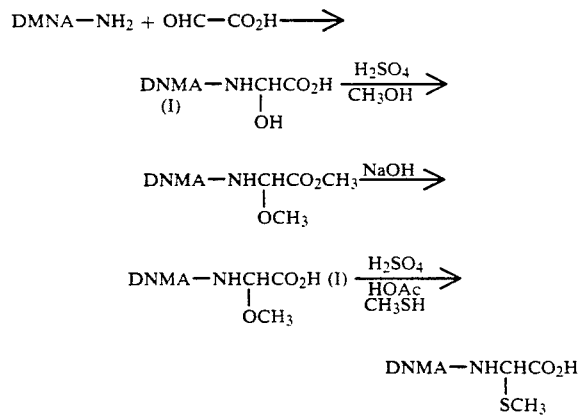

SCHEME II

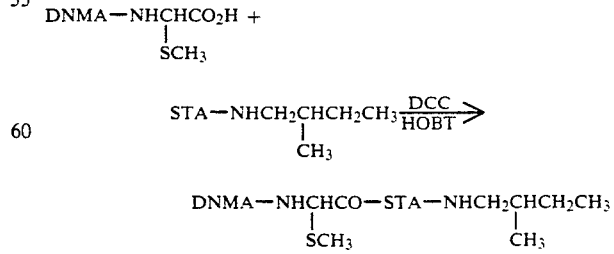

SCHEME III

DNMA—NHCHCO—STA—NHCH$_2$CH(CH$_3$)CH$_2$CH$_3$ $\xrightarrow[\text{NH}_3]{\text{HgCl}_2}$
|
SCH$_3$ DNMA—NHCHCO—STA—NHCH$_2$CH(CH$_3$)CH$_2$CH$_3$ $\xrightarrow[\text{Et}_3\text{N}]{\text{ClCO}_2\text{Et}}$ DNMA—NHCHCO—STA—NHCH$_2$CH(CH$_3$)CH$_2$CH$_3$
|                                                                                                |
NH$_2$                                                                                          NHC—OEt
                                                                                                 ‖
                                                                                                 O The intermediates of Scheme I are novel and are prepared by an adaptation of a method described by U. Zollner and D. Ben-Ishai, Tetrahedron 31, 863(1975). Those compounds bearing an α-oxygen atom are prepared in the following manner. DNMA—NH$_2$ and glyoxylic acid hydrate are heated in acetone for 4 to 24 hours, giving the α-OH compound I. I is dissolved in the appropriate alcohol, cooled to 0°, and treated with concentrated H$_2$SO$_4$. The mixture is allowed to warm to room temperature for 8 to 24 hours giving the corresponding ester of the α-alkoxy compound. The exter is hydrolyzed at room temperature for 2 to 24 ours with strong bases as NaOH, KOH, or LiOH, giving the desired product.

The α-sulfur atom derivatives may also be prepared from the α-hydroxy compound I. In this procedure I is dissolved in HOAc, cooled to 0°, and treated with concentrated H$_2$SO$_4$ and the appropriate mercaptan. After stirring at room temperature for 1 to 4 days, the α-mercapto derivative can be isolated.

The novel α-amino derivatives can be prepared according to Scheme III from the completed peptide. The peptide is dissolved in THF, cooled to −60° and treated with mercuric chloride. The appropriate amine is then added and the mixture is allowed to warm to room temperature over 4 to 24 hours, giving the desired product. This procedure is an adaptation of that described by M. G. Bock, R. M. DiPardo, and R. Freidinger, J. Org. Chem. 51, 3718 (1986).

Scheme II describes preparing the completed peptide. The appropriate DNMA acylated α-heteroatom amino acid derivative is coupled to STA—NHCH$_2$CH(CH$_3$)CH$_2$CH$_3$ in an inert solvent such as DMF, THF, CHCl$_3$, CH$_2$Cl$_2$, or EtOAc at −5° to 25° for 4 to 24 hours, in the presence of DCC and HOBT.

αOxygen-containing compounds of formula I are prepared by:

(a) reacting DNMA—NH$_2$ with glyoxylic acid to produce DNMA—NHCH(OH)CO$_2$H, (b) reacting the product of step (a) with an alcohol to product DNMA—NHCH(OR$_1$)CO$_2$R$_1$, wherein R$_1$ is lower alkyl, lower alkenyl, lower alkynyl, aryl, heteroaryl, aralkyl, (CH$_2$)$_n$—NHR$_2$, wherein n is an integer of from 2 to 4, and R$_2$ is C—NHCH$_3$, C—NHCH$_3$, C—NHNO$_2$, C—SCH$_3$,
‖         ‖         ‖         ‖
O         S         NH        NCN C—NHCH$_3$, C—R$_3$, C—CHNHR$_5$,
‖         ‖       ‖  |
NCN       O       O  R$_4$

C—CH$_2$CH$_2$NHC—R$_5$,
‖              ‖
O              O wherein R$_3$ is hydrogen, lower alkyl, or aryl, R$_4$ is H, lower alkyl or aralkyl, R$_5$ is C—NHCH$_3$, C—NHCH$_3$, C—NHNO$_2$, C—SCH$_3$,
‖         ‖         ‖         ‖
O         S         NH        NCN

C—NHCH$_3$, C—R$_6$
‖         ‖
NCN       O wherein R$_6$ is hydrogen, lower alkyl or aryl, (c) hydrolyzing the product of step (b) to DNMA—NHCH(OR$_1$)CO$_2$H wherein R$_1$ is as defined above, and (d) reacting the product the step (c) with the desired fragment to produce a peptide of formula I, and converting, if desired, to a pharmaceutically acceptable salt thereof.

α-Sulphur-containing compounds of formula I are prepared by:

(a) reacting DNMA—NH$_2$ with glyoxylic acid to produce DNMA—NHCH(OH)CO$_2$H, (b) reacting the product of step (a) with a mercaptan to produce DNMA—NHCH(SR$_1$)CO$_2$H wherein R$_1$ is lower alkyl, lower alkyenyl, lower alkynyl, aryl, heteroaryl, aralkyl, (CH$_2$)$_n$—NHR$_2$, wherein n is an integer of from 2 to 4, and R$_2$ is C—NHCH$_3$, C—NHCH$_3$, C—NHNO$_2$, C—SCH$_3$,
‖         ‖         ‖         ‖
O         S         NH        NCN C—NHCH$_3$, C—R$_3$, C—CHNHR$_5$,
‖         ‖       ‖  |
O         O       O  R$_4$

C—CH$_2$CH$_2$NHC—R$_5$,
‖              ‖
O              O wherein R$_3$ is hydrogen, lower alkyl, or aryl, R$_4$ is H, lower alkyl or aralkyl, R$_5$ is C—NHCH$_3$, C—NHCH$_3$, C—NHNO$_2$, C—SCH$_3$,
‖         ‖         ‖         ‖
O         S         NH        NCN

C—NHCH$_3$, C—R$_6$
‖         ‖
NCN       O wherein R$_6$ is hydrogen, lower alkyl or aryl, (c) coupling the product of step (b) with STA—NHCH$_2$CH(CH$_3$)CH$_2$CH$_3$ to produce the corresponding DNMA—NHCH(SR$_1$)CO—S-TA—NHCH$_2$CH(CH$_3$)CH$_2$CH$_3$ wherein R$_1$ is as above, and converting, if desired, to a pharmaceutically acceptable salt thereof.

α-Amino-containing compounds of formula I are prepared by treating DNMA—NHCH(SR$_1$)CO—S-

TA—NHCH$_2$CH(CH$_3$)CH$_2$CH$_3$ with mercuric chloride in the presence of an amine to produce a desired compound of formula I and converting, if desired, to a pharmaceutically acceptable salt thereof.

Using BBSP—NH$_2$, the amide derived from 2-benzyl-3-(t-butylsulfonyl)propionic acid (EP-236,734) in place of DNMA—NH$_2$ and following the routes outlined in Schemes I, II, and III, certain peptides of the present invention can be prepared. Likewise, using Z—BMA—NH$_2$, the amide derived from 3-(benzyloxycarbonylamino)-3-methylbutanoic acid (EP-229,667), and following the routes outlined in Schemes I, II, and III, certain precursors of other target peptides of the present invention can be prepared. Removal of the benzyloxycarbonyl group gives certain other peptides of the present invention.

The strategy of peptide chain assembly and selection and removal of protecting groups is discussed in Chapter 1, "The Peptide Bond", in "The Peptides, Analysis, Synthesis, Biology," E. Gross and J. Meienhofer, Eds., Academic Press, New York, NY, 1979, Vol. 1, pp. 42-44.

The DCC/HOBT method of coupling is well known to those skilled in the art and is discussed in Chapter 5, "The Carbodiimide Method" by D. H. Rich and J. Singh in "The Peptides. Analysis, Synthesis, Biology," E. Gross and J. Meienhofer, Eds., Academic Press, New York, NY, 1979, Vol. 1, pp. 241-261.

Peptide coupling depends on activating the carboxyl group of the protected amino acid prior to condensing it with another peptide containing a free amino terminus. In addition to the DCC coupling method described above, other methods of activating the carboxyl group of a protected amino acid include:

1) The azide method—described in Chapter 4 of the above reference.
2) The mixed anhydride method—described in Chapter 6 of the above reference.
3) The active ester method—described in Chapter 3 of the above reference.

The acyl groups derived from the substituted succinic acid amides may be prepared as follows. 1-Naphthaldehyde is reacted with diethyl succinate in a Stobbe condensation, and the corresponding di-acid is converted to the anhydride with acetic anhydride. Treatment with the appropriate amine gives 2-(1-naphthylmethylene)-3-(substituted aminocarbonyl) propionic acid. Catalytic hydrogenation gives the desired 2-(1-naphthylmethyl)-3-(substituted aminocarbonyl)propionic acid. This acid may be condensed with suitably protected amino acids using the coupling methods known to peptide chemistry, for example, the carbodiimide method. This is discussed in European Application Publication No. 206,807 and European Application Publication No. 200,406.

The compounds of the present invention are useful for treating renin-associated hypertension, congestive heart failure, and hyperaldosteronism. They are also useful as diagnostic tools for determining the presence of renin-associated hypertension or hyperaldosteronism.

The term lower alkyl refers to straight or branched chain hydrocarbon radicals containing from 1 to 10 carbon atoms including but not limited to methyl, ethyl, n-propyl, isopropyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl and the like.

Lower alkenyl means a straight or branched chain hydrocarbon radical of from 1 to 10 carbon atoms containing a double bond. This includes but is not limited to allyl and methylallyl.

Lower alkynyl means a straight or branched chain hydrocarbon radical of from 1 to 10 carbon atoms containing a triple bond. This includes but is not limited to propargyl.

Aryl means phenyl, naphthyl or other aromatic groups, including mono- or bicyclic, which may be substituted, especially monosubstituted, by F, Cl, Br, I, CF$_3$, OH, OR, or R, wherein R is lower alkyl.

Heteroaryl means aromatic heterocyclic rings containing at least one heteroatom selected from O, S, and N and from 3 to 5 carbon atoms including but not limited to thiazoles and imidazoles.

Aralkyl is as described above for alkyl and aryl, including but not limited to benzyl.

Substituted alkyl includes but is not limited to such groups as hydroxy and halogen.

Pharmaceutical compositions which comprise an effective amount of the compound in combination with a pharmaceutically acceptable carrier are part of the present invention. An important aspect of the present invention is a method of treating renin-associated hypertension in a mammal which comprises administering a pharmaceutical composition containing an effective amount of a compound of the invention in combination with a pharmaceutically acceptable carrier to the mammal.

Another equally important aspect of the present invention is a method of treating hyperaldosteronism in a mammal which comprises administering a pharmaceutical composition containing an effective amount of a compound of the invention in combination with a pharmaceutically acceptable carrier to the mammal.

Yet another important aspect of the present invention is method of treating congestive heart failure in a mammal which comprises administering a pharmaceutical composition containing an effective amount of a compound of the invention in combination with a pharmaceutically acceptable carrier.

The effectiveness of the aforementioned compounds is determined by a test for in vitro renin inhibitory activity. This activity is determined by a standard radioimmunoassay for angiotensin I. In this assay the enzyme, renin, incubated for 2 hours at 37° in the presense of a substrate, angiotensinogen, generates the product, angiotensin I. Test compounds are added to the incubation mixture. Relative activity is reported as the percent inhibition at $10^{-6}$ molar concentration.

TABLE II

| Inhibition Compound | Activity % @ $10^{-6}$ M |
|---|---|
| DNMA—NHCH(OCH$_3$)CO—STA—NHCH$_2$CH(CH$_3$)CH$_2$CH$_3$ | 90 |
| DNMA—NHCH(SCH$_3$)CO—STA—NHCH$_2$CH(CH$_3$)CH$_2$CH$_3$ | 86 |
| DNMA—NHCH(SOCH$_3$)CO—STA—NHCH$_2$CH(CH$_3$)CH$_2$CH$_3$ | 35 |
| DNMA—NHCH(SCH(CH$_3$)$_2$)CO—STA—NHCH$_2$CH(CH$_3$)CH$_2$CH$_3$ | 87 |

TABLE II-continued

| Inhibition Compound | Activity % @ $10^{-6}$ M |
|---|---|
| (fast isomer) DNMA—NHCH(SCH(CH$_3$)$_2$)CO—STA—NHCH$_2$CH(CH$_3$)CH$_2$CH$_3$ | 26 |
| (slow isomer) DNMA—NHCH(NH$_2$)CO—STA—NHCH$_2$CH(CH$_3$)CH$_2$CH$_3$ | 9 |
| (fast isomer) DNMA—NHCH(NH$_2$)CO—STA—NHCH$_2$CH(CH$_3$)CH$_2$CH$_3$ | 54 |
| (slow isomer) DNMA—NHCH(NHCO$_2$Et)CO—STA—NHCH$_2$CH(CH$_3$)CH$_2$CH$_3$ | 40 |
| DNMA—NHCH(OC$_2$H$_5$)CO—STA—NHCH$_2$CH(CH$_3$)CH$_2$CH$_3$ | 100 |
| (fast isomer) DNMA—NHCH(OC$_2$H$_5$)CO—STA—NHCH$_2$CH(CH$_3$)CH$_2$CH$_3$ | 15 |
| (slow isomer) DNMA—NHCH(NH(CH$_2$)$_3$NHCSNHCH$_3$)CO—STA—NHCH$_2$CH(CH$_3$)CH$_2$CH$_3$ | 36 |
| DNMA—NHCH(NHCOCH$_3$)CO—STA—NHCH$_2$CH(CH$_3$)CH$_2$CH$_3$ | 39 |
| DNMA—NHCH(NHPh)CO—STA—NHCH$_2$CH(CH$_3$)CH$_2$CH$_3$ | 56 |
| DNMA—NHCH(SPh)CO—STA—NHCH$_2$CH(CH$_3$)CH$_2$CH$_3$ | 40 |
| DNMA—NHCH(N(CH$_3$)$_2$)CO—STA—NHCH$_2$CH(CH$_3$)CH$_2$CH$_3$ | 55 |
| (slow isomer) DNMA—NHCH(NHCH(CH$_3$)$_2$)CO—STA—NHCH$_2$CH(CH$_3$)CH$_2$CH$_3$ | 60 |
| (slow isomer) DNMA—NHCH(NHC$_2$H$_5$)CO—STA—NHCH$_2$CH(CH$_3$)CH$_2$CH$_3$ | 71 |
| (slow isomer) O⟨N—SO$_2$—PHE—NHCH(OC$_2$H$_5$)CO—CYSTA—NHCH$_2$CH$_2$N⟩O (slow isomer) | 57 |
| O⟨N—SO$_2$—PHE—NHCH(OC$_2$H$_5$)CO—CYSTA—NHCH$_2$CH$_2$N⟩O (mixture of isomers) | 100 |

As can be seen from the above table, the compounds of the present invention have a significant effect on the activity of renin and thus are useful for the treatment of hypertension, congestive heart failure, and hyperaldosteronism.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

The compounds of the present invention may be administered orally, buccally, parenterally, by inhalation spray, rectally or topically in dosage unit formulations containing conventional nontoxic pharmaceutically acceptable carriers, adjuvants and vehicles as desired. The term parenteral as used herein includes subcutaneous injections, intravenous, intramuscular, intrasternal injection or infusion techniques.

For preparing suppositories, a low melting wax such as a mixture of fatty acid glycerides or cocoa butter is first melted, and the active ingredient is dispersed homogeneously therein by stirring. The molten homogeneous mixture is then poured into convenient sized molds, allowed to cool, and thereby solidify.

Liquid form preparations include solutions, suspensions, and emulsions. As an example may be mentioned water or water/propylene glycol solutions for parenteral injection. Liquid preparations can also be formulated in solution in aqueous polyethyleneglycol solution. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerin, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient. The compositions can, if desired, also contain other compatible therapeutic agents.

In therapeutic use as renin inhibitors, the mammalian dosage range for a 70 kg subject is from 1 to 1500 mg per day or preferably 25 to 750 mg per day optionally in divided portions. The dosages, however, may be varied depending upon the requirements of the patient, the severity of the condition being treated and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following examples are provided to enable one skilled in the art to practice the present invention. These examples are not intended in any way to limit the scope of the invention but are illustrative thereof.

EXAMPLE 1

DNMA—NHCH(OCH$_3$)CO—S-
TA—NHCH$_2$CH(CH$_3$)CH$_2$CH$_3$

DNMA—NHCH(OCH$_3$)CO$_2$H (1.30 g, 3.04 mmole) was dissolved in 30 ml CH$_2$Cl$_2$ and cooled to 0°. A solution of HOBT.H$_2$O (0.42 g, 3.13 mmole) in 3 ml DMF was added, followed by DCC (0.65 g, 3.13 mmole). A solution of STA—NHCH$_2$CH(CH$_3$)CH$_2$CH$_3$ (0.74 g, 3.04 mmole) in 15 ml CH$_2$Cl$_2$ was added, followed by stirring overnight at 23°. The resulting suspension was filtered and the filtrate evaporated to an oil and taken up in EtOAc. The solution was washed with 1N citric acid, saturated NaCl, saturated NaHCO$_3$, and saturated NaCl, followed by drying over MgSO$_4$. The solution was evaporated under reduced pressure to a foam which was chromatographed on silica gel, eluting with EtOAc/CHCl$_3$(1/1). The product was obtained as a white foam, 1.5 g, 75.4% yield. The structure was confirmed by NMR and mass spectroscopy.

Calcd. for C$_{40}$H$_{51}$N$_3$O$_5$ (MW 653.87): C, 73.48; H, 7.86; N, 6.43 Found: C, 73.34; H, 7.94; N, 6.35

EXAMPLE 2

DNMA—NHCH(SCH$_3$)CO—S-
TA—NHCH$_2$CH(CH$_3$)CH$_2$CH$_3$

DNMA—NHCH(SCH$_3$)CO$_2$H (5.86 g, 13.2 mmole) was dissolved in 100 ml CH$_2$Cl$_2$ and cooled to 0°. A solution of HOBT.H$_2$O (1.84 g, 13.6 mmole) in 6 ml DMF was added. DCC (2.81 g, 13.6 mmole) was added, followed by a solution of STA—NHCH$_2$CH(CH$_3$)CH$_2$CH$_3$ (3.22 g, 13.2 mmole) in 25 ml of CH$_2$Cl$_2$. After stirring at 23° overnight, the mixture was filtered, and the filtrate evaporated to an oil. The oil was dissolved in EtOAc, the solution filtered, and the filtrate washed with 1N citric acid, saturated NaCl, saturated NaHCO$_3$, and saturated NaCl. The organic phase was dried over MgSO$_4$, and evaporated under reduced pressure to a white foam. The foam was chromatographed on silica gel, eluting with EtOAc/CHCl$_3$ (1/1), giving the product as a white foam, 7.37 g, 83% yield. The structure was confirmed by NMR and mass spectroscopy.

Calcd. for C$_{40}$H$_{51}$N$_3$O$_4$S.0.125 H$_2$O (MW 672.19): C, 71.47; H, 7.68; N, 6.25; H$_2$0, 0.33; S, 4.77 Found: C, 71.16; H, 7.55; N, 6.21; H$_2$0, 0.33; S, 4.72

EXAMPLE 3

DNMA—NHCH(SOCH$_3$)CO—S-
TA—NHCH$_2$CH(CH$_3$)CH$_2$CH$_3$

DNMA—NHCH(SCH$_3$)CO—S-
TA—NHCH$_2$CH(CH$_3$)CH$_2$CH$_3$ (1.5 g, 2.24 mmole) was dissolved in 25 ml MeOH, to which was added a solution of NaIO$_4$ (1.01 g, 4.68 mmole) in 10 ml H$_2$O. After warming to 50° for 2 hours, the mixture was evaporated to an oil. The oil was taken into EtOAc and extracted with H$_2$O, 10% sodium bisulfite solution, saturated NaHCO$_3$ and saturated NaCl. After drying over MgSO$_4$, the mixture was evaporated under reduced pressure to a foam. The foam was chromatographed on silica gel, eluting with EtOAc/CHCl$_3$ (3/1). Combination of the appropriate factions gave the product as a white foam, 0.85 g. The structure was confirmed by NMR and mass spectroscopy.

Calcd. for (MW 685.93): C, 70.04; H, 7.49; N, 6.13; S, 4.67 Found: C, 70.06; H, 7.54; N, 6.03; S, 4.51

EXAMPLES 4 AND 5

DNMA—NHCH(SCH(CH$_3$)$_2$)CO—S-
TA—NHCH$_2$CH(CH$_3$)CH$_2$CH$_3$

DNMA—NHCH(SCH(CH$_3$)$_2$)CO$_2$H (7.48 g, 15.9 mmole) was dissolved in 130 ml CH$_2$Cl$_2$. A solution 16.3 mmole) in 4 ml DMF was added, and the mixture was cooled to 0°. DCC (3.37 g, 16.3 mmole) was added, followed by a solution of STA—NHCH$_2$CH(CH$_3$)CH$_2$CH$_3$ (3.87 g, 15.9 mmole) in 25 ml CH$_2$Cl$_2$. The mixture was stirred at 23° overnight, filtered, and the filtrate evaporated to an oil, which was taken up in EtOAc and filtered. The filtrate was washed with 1N citric acid, saturated NaCl, saturated NaHCO$_3$, and saturated NaCl. The solution was dried over MgSO$_4$ and evaporated under reduced pressure to a foam which was chromatographed on silica gel, eluting with EtOAc/CHCl$_3$ (1/1). Fractions containing the faster eluting isomer were combined, giving the product as a white foam, 1.91 g. The structure was confirmed by NMR and mass spectroscopy.

Calcd. for C$_{42}$H$_{55}$N$_3$O$_4$S.0.06 CHCl$_3$ (MW 705.45): C, 71.61; H, 7.86; N, 5.95; S, 4.54; Cl, 0.94. Found: C, 71.53; H, 8.13; N, 6.18; S, 4.40; Cl, 0.74

Fractions containing the slower eluting diastereomer were combined giving 1.80 g of the product as a foam, identified by NMR and mass spectroscopy.

Calcd. for C$_{42}$H$_{55}$N$_3$O$_4$S. 0.5 H$_2$O (MW 706.97): C, 71.35; H, 7.98; N, 5.94; S, 4.53; H20, 1.27. Found: C, 71.50; H, 7.83; N, 5.91; S, 4.68; H20, 1.01

EXAMPLES 6 AND 7

DNMA—NHCH(NH$_2$)CO—S-TA—NHCH$_2$CH(CH$_3$)CH$_2$CH$_3$

DNMA—NHCH(SCH$_3$)CO—S-TA—NHCH$_2$CH(CH$_3$)CH$_2$CH$_3$ (2.91 g, 4.34 mmole) was dissolved in 100 ml THF, and mercuric chloride (1.76 g, 6.48 mmole) was added. After cooling to −60°, the mixture was saturated with anhydrous NH$_3$ gas. After warming to 23° overnight, the mixture was recooled and saturated with NH$_3$ gas again, and allowed to warm to 23° over 4 hours. The mixture was evaporated to a foam, taken into Et$_2$O and filtered. The filtrate was briefly purged with HCl gas until acidic to wet litmus. A white solid precipitated, which was filtered, washed with Et$_2$O, dried, and chromatographed on silica gel, eluting with a gradient of 0-5% MeOH in CHCl$_3$ Combination of the fractions containing the faster eluting isomer yielded a foam which was dissolved in Et$_2$O and purged briefly with HCl gas. The resulting solid was filtered, washed with Et$_2$O and dried giving the product as a white solid, 0.87 g. The structure was confirmed by NMR and mass spectroscopy.

Calcd. for C$_{39}$H$_{50}$N$_4$O$_4$.1.1 HCl.0.5 H$_2$O (MW 687.97): C, 68.09; H, 7.63; N, 8.14; Cl, 5.67; H20, 1.31. Found: C, 68.50; H, 7.65; N, 8.06; Cl, 5.92; H$_2$, 1.69

Fractions containing the slower eluting diastereomer were similarly treated, giving a white solid, 0.92 g. The structure was confirmed by NMR and mass spectroscopy.

Calcd. for C$_{39}$H$_{50}$N$_4$O$_4$ .1.2 HCl.0.6 H$_2$O(MN 693.42): C, 67.55; H, 7.61; N, 8.08; Cl, 6.13; H20, 1.56. Found: C, 68.37; H, 7.78; N, 8.07; Cl, 6.33; H20, 1.53

Fractions containing a mixture both isomers were evaporated to a white foam, 0.35 g, which was used in the preparation of Example 8.

EXAMPLE 8

DNMA—NHCH(NHCO$_2$Et)CO—S-TA—NHCH$_2$CH(CH$_3$)CH$_2$CH$_3$

DNMA—NHCH(NH$_2$)CO—S-TA—NHCH$_2$CH(CH$_3$)CH$_2$CH$_3$ (0.35 g, 0.5 mmole) as a mixture of diastereomers, was dissolved in 20 ml THF. Et$_3$N (0.078 ml, 0.56 mmole) was added, followed by ethyl chloroformate (0.055 ml, 0.56 mmole). After stirring 2 hours at 23°, the mixture was filtered, the collected solid washed with THF, and the filtrate evaporated to a foam. The residue was taken up in EtOAc, washed with 1N citric acid, saturated NaCl, saturated NaHCO$_3$, and saturated NaCl. The organic phase was dried over MgSO$_4$ and evaporated under reduced pressure giving the product as a foam, 0.38 g. The structure was confirmed by NMR and mass spectroscopy.

Calcd. for C$_{42}$H$_{54}$N$_4$O$_6$ (MW 710.92): C, 70.96; H, 7.65; N, 7.88. Found: C, 71.22; H, 7.78; N, 7.92

EXAMPLES 9 AND 10

DNMA—NHCH(OC$_2$H$_5$)CO—S-TA—NHCH$_2$CH(CH$_3$)CH$_2$CH$_3$

DNMA—NHCH(OC$_2$H$_5$)CO$_2$H (1.20 g, 2.72 mmole) was dissolved in 50 ml CH$_2$Cl$_2$. A solution of HOBT.H$_2$O (0.38 g, 2.8 mmole) in 4 ml DMF was added, followed by cooling the mixture to 0°. STA—NHCH$_2$CH(CH$_3$)CH$_2$CH$_3$ (0.67 g, 2.72 mmole) dissolved in 20 ml CH$_2$Cl$_2$ was added, followed by the addition of DCC (0.58 g, 2.8 mmole). The mixture was stirred and allowed to warm to 23° overnight. The mixture was filtered, evaporated to a syrup, and taken up into EtOAc. The mixture was again filtered, and washed with 1 N citric acid, saturated NaCl, saturated NaHCO$_3$, and saturated NaCl. The mixture was dried over MgSO$_4$, filtered, and evaporated to a foam, 1.86 g. The foam was chromatographed on silica gel eluting with EtOAc/CHCl$_3$ (1/1). Combination of fractions containing the faster eluting isomer gave a foam which was recrystallized from Et$_2$O giving 0.45 g of the product as a solid. The structure was confirmed by NMR and mass spectroscopy.

Calcd. for C$_{41}$H$_{53}$N$_3$O$_5$ (MW 667.90): C, 73.73; H, 7.99; N, 6.29. Found: C, 73.57; H, 7.89; N, 6.38

The slower eluting isomer was similarly obtained as a crystalline solid, 0.48 g. The structure was confirmed by NMR and mass spectroscopy.

Calcd. for C$_{41}$H$_{53}$N$_3$O$_5$ (MW 667.90): C, 73.73; H, 7.99; N, 6.29. Found: C, 73.73; H, 7.98; N, 6.35

EXAMPLE 11

DNMA—NHCH(NH(CH$_2$)$_3$NHCSNHCH$_3$-)CO—STA—NHCH$_2$CH(CH$_3$)CH$_2$CH$_3$

DNMA—NHCH(NH(CH$_2$  )CO—S-TA—NHCH$_2$CH(CH$_3$)CH$_2$CH$_3$ (2.97 g, 4.35 mmole) was dissolved in 75 ml CH$_2$Cl$_2$ and methylisothiocyanate (0.32 g, 4.44 mmole) was added. After stirring at 23° overnight, the mixture was evaporated to a foam and dissolved in EtOAc. The solution was washed with 1N HCl, saturated NaCl, 1N NaOH, and saturated NaCl. The solution was dried over MgSO$_4$ and evaporated under reduced pressure to give the crude product as a white foam, 3.13 g. The crude product was chromatographed on silica gel eluting with CHCl$_3$/EtOAc (40/60) with a gradient to 15% MeOH. The product was recovered as a white foam, 2.41 g. Trituration with Et$_2$O gave 1.9 g of a white solid. The structure was confirmed by NMR and mass spectroscopy.

Calcd. for C$_{44}$H$_{60}$N$_6$O$_4$S.0.75H20.0.08CHCl$_3$ (MW 792.13): C, 66.83; H, 7.83; N, 10.61; S, 4.05; H20, 1.70; Cl, 1.07. Found: C, 67.77; H, 7.83; N, 10.40; S, 4.13; H20, 1.69; Cl, 1.24.

EXAMPLE 12

DNMA—NHCH(NHCOCH$_3$)CO—S-
TA—NHCH$_2$CH(CH$_3$)CH$_2$CH$_3$

DNMA—NHCH(NH$_2$)CO—S-
TA—NHCH$_2$CH(CH$_3$)CH$_2$CH$_3$.HCl (0.73 g, 1.05 mmole) of the slow isomer (Example 7) was suspended in 25 ml of CH$_2$Cl$_2$ and treated with 0.35 ml (1.08 mmole) of Et$_3$N causing solution. This was then treated with 0.09 ml (1.08 mmole) of acetyl chloride and stirred at room temperature for 2.5 hours. The mixture was filtered and the solvent removed under reduced pressure. The solid residue was taken up in EtOAc and washed with H$_2$O, 1N citric acid, and saturated NaCl. Drying and removal of the solvent under reduced pressure gave a paste which was triturated with Et$_2$O giving 0.62 g of the product as a white powder. The structure was confirmed by NMR and mass spectroscopy.

Calcd. for C$_{41}$H$_{52}$N$_4$O$_5$ (MW 680.89): C, 72.32; H, 7.70; N, 8.23. Found: C, 72.08; H, 7.63; N, 825

EXAMPLE 13

DNMA—NHCH(NHPh)CO—S-
TA—NHCH$_2$CH(CH$_3$)CH$_2$CH$_3$

DNMA—NHCH(SCH(CH$_3$)$_2$)CO—S-
TA—NHCH$_2$CH(CH$_3$)CH$_2$CH$_3$, a mixture of diastereomers, (2.20 g, 3.15 mmole) was dissolved in 100 ml dry THF and aniline (0.88 g, 9.45 mmole) was added. HgCl$_2$ (1 3 g, 4.75 mmole) was added and the solution was stirred at 23° overnight. An additional amount of HgCl$_2$ was added (0.48 g, 5.15 mmole) followed by stirring at 23° for two days. The mixture was filtered and the solvent evaporated leaving a solid. This was mixed with EtOAc, filtered, and the filtrate washed with 1N HCl, saturated NaCl, 1N NaOH, and saturated NaCl. The EtOAc phase was dried over MgSO$_4$, and evaporated under reduced pressure to a yellow foam, 2.23 g. Chromatography on silica gel, eluting with EtOAc/CHCl$_3$ (1/1) gave 1.85 g of the product as a white foam. The structure was confirmed by NMR and mass spectroscopy.

Calcd. for C$_{45}$H$_{54}$N$_4$O$_4$.0.25EtOAc.0.25H$_2$O (MW 741.49): C, 74.51; H, 7.68; N, 7.56; H$_2$O, 0.61. Found: C, 74.25; H, 7.59; N, 7.52; H$_2$O, 0.62

EXAMPLE 14

DNMA—NHCH(SPh)CO—S-
TA—NHCH$_2$CH(CH$_3$)CH$_2$CH$_3$

DNMA—NHCH(SPh)CO$_2$H (1.77 g, 3.50 mmole) was dissolved in 75 ml CH$_2$Cl$_2$ and cooled to 0°. A solution of HOBT.H$_2$O (0.52 g, 3.85 mmole) in 6 ml DMF was added. DCC (0.79 g, 3.85 mmole) was added, followed by a solution of STA—NHCH$_2$CH(CH$_3$)CH$_2$CH$_3$ (0.91 g, 3.74 mmole) in 20 ml CH$_2$Cl$_2$. After stirring at 23° overnight, the mixture was filtered, and the filtrate evaporated to an oil. The oil was dissolved in EtOAc, the solution filtered, and the filtrate washed with 1N citric acid, saturated NaCl, saturated NaHCO$_3$ and saturated NaCl. The organic phase was dried over MgSO$_4$, and evaporated under reduced pressure to a white foam, 2.66 g. The foam was chromatographed on silica gel, eluting with EtOAc/CHCl$_3$ (1/1) and giving the product as a white foam, 2.0 g. The structure was confirmed by NMR and mass spectroscopy.

Calcd. for C$_{45}$H$_{53}$N$_3$O$_4$S.0.25H$_2$O (MW 736.51): C, 73.39; H, 7.32; N, 5.70; S, 4.35; H$_2$O, 0.61. Found: C, 73.10; H, 7.48; N, 5.94; S, 4.68; H$_2$O, 0.33.

EXAMPLE 15

DNMA—NHCH(N(CH$_3$)($_2$)CO—S-
TA—NHCH$_2$CH(CH$_3$)CH$_2$CH$_3$

DNMA—NHCH(SCH$_3$)CO—S-
TA—NHCH$_2$CH(CH$_3$)CH$_2$CH$_3$ (1.54 g, 2.3 mmole) was dissolved in 50 ml dry THF, and dimethylamine (5 ml) was added. HgCl$_2$ (0.94 g, 3.45 mmole) was added and the solution was refrigerated at 4° for two days. The excess dimethylamine was removed in vacuo, the mixture filtered, and the solvent evaporated giving a gum. The gum was resuspended in EtOAc, the suspension filtered, and the filtrate washed with 1N HCl, saturated NaCl solution, and 1N NaOH. An orange precipitate formed, which was filtered off. The organic phase of the filtrate was washed with saturated NaCl, dried over MgSO$_4$, and evaporated under reduced pressure to a white foam, 1.49 g. Chromatography on silica gel, eluting with CHCl$_3$/EtOAc/MeOH (35/55/10) separated the mixture into a faster eluting diastereomer and a slower eluting diastereomer. The product, the slower eluting isomer, was obtained as a white foam, 0.82 g. The structure was confirmed by NMR and mass spectroscopy.

Calcd. for C$_{41}$H$_{54}$N$_4$O$_4$ (MW 666.91): C, 73.84; H, 8.16; N, 8.40. Found: C, 73.59; H, 8.30; N, 8.20.

EXAMPLE 16

DNMA—NHCH(NHCH(CH$_3$)$_2$)CO—S-
TA—NHCH$_2$CH(CH$_3$)CH$_2$CH$_3$

DNMA—NHCH(SCH$_3$)CO—S-
TA—NHCH$_2$CH(CH$_3$)CH$_2$CH$_3$ (1.54 g, 2.3 mmole) was dissolved in 50 ml dry THF, and isopropylamine (1.0 ml) was added. HgCl$_2$ (0.94 g, 3.45 mmole) was added and solution occurred. After stirring at 23° for 2 hours, a precipitate formed and the mixture was refrigerated at 4° for two days. The mixture was filtered, evaporated to a foam and resuspended in EtOAc. The mixture was filtered, and the filtrate was washed with 1N HCl, saturated NaCl, and 1N NaOH. An orange precipitate formed which was filtered off. The organic phase was washed with saturated NaCl, dried over MgSO$_4$, and evaporated under reduced pressure to a white foam, 1.62 g. Chromatography on silica gel, eluting with CHCl$_3$/EtOAc/MeOH (35/55/10), separated the mixture into faster and slower eluting diastereomers. The product, the slower eluting diastereomer, was obtained as a crystalline solid, 0.73 g. The structure was confirmed by NMR and mass spectroscopy.

Calcd. for C$_{41}$H$_{54}$N$_4$O$_4$.0.15H$_2$O (MW 669.61): C, 73.54; H, 8.17; N, 8.37; H$_2$O, 0.40. Found: C, 73.18; H, 8.15; N, 8.33; H$_2$O, 0.27.

EXAMPLE 17

DNMA—NHCH(NHC$_2$H$_5$)CO—S-
TA—NHCH$_2$CH(CH$_3$)CH$_2$CH$_3$

DNMA—NHCH(SCH₃)CO—S-TA—NHCH₂CH(CH₃)CH₂CH₃) 1.54 g, 2.3 mmole) was dissolved in 50 ml dry THF, and ethylamine (5 ml) was added. HgCl₂ (0.94 g, 3.45 mmole) was added, and solution occurred followed by solid precipitation. After stirring at 23° overnight, the mixture was filtered, excess amine removed under vacuum, and the mixture filtered again. The filtrate was evaporated under reduced pressure and the residue was resuspended in EtOAc. The mixture was filtered and the filtrate was washed with 1N HCl, saturated NaCl, 1N NaOH, and saturated NaCl. The solution was dried over MgSO₄ and evaporated under reduced pressure to a white foam, 1.61 g. Chromatography on silica gel, eluting with CHCl₃/EtOAc/MeOH (35/55/10) separated the mixture into faster and slower eluting diastereomers. The product, the slower eluting diastereomer, was obtained as a white foam, 0.96 g. The structure was confirmed by NMR and mass spectroscopy.

Calcd. for C₄₂H₅₆N₄O₄.0.1CHCl 0.25H₂O (MW 697.43): C, 72.50; H, 8.19; N, 8.03; H20, 0.65; Cl, 1.52. Found: C, 72.86; H, 8.35; N, 7.85; H20, 0.62; Cl, 1.54.

EXAMPLES 18 AND 19

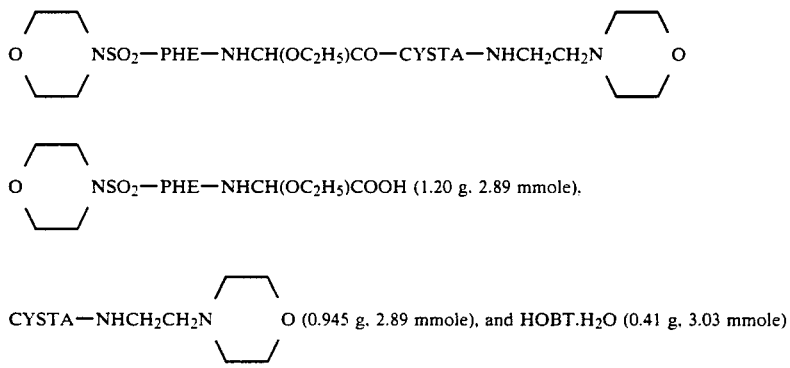

were dissolved in 50 ml CH₂Cl₂ and cooled to 0°. DCC (0.64 g, 3.1 mmole) was added, and the mixture was allowed to warm to 23° overnight. The mixture was concentrated to 25 ml in volume under reduced pressure, and filtered to remove insoluble matter. The filtrate was evaporated, and the residue was resuspended in EtOAc. A solid precipitated, which was again filtered. The solid thus recovered was found to be pure, slower eluting diastereomer, 0.41 g. The structure was confirmed by NMR and mass spectroscopy.

Calcd. for C₃₄H₅₆N₆O₉S (MW 724.92): C, 56.33; H, 7.79; N, 11.59; S, 4.42. Found: C, 56.48; H, 7.94; N, 11.66; S, 4.49.

The filtrate from removal of some of the slower moving diastereomer was washed with saturated NaHCO₃ and saturated NaCl. Drying over MgSO₄ and removing the solvent under reduced pressure gave a foam, 1.67 g. The foam was chromatographed on silica gel, eluting with a gradient of 2 to 5% MeOH in CHCl₃, and giving a mixture of the faster and slower eluting diastereomers as a foam, 1.34 g. The structure was confirmed by NMR and mass spectroscopy.

Calcd. for C₃₄H₅₆N₆O₉S.0.2CHCl₃ 0.6H20 (MW 759.61) C, 54.08; H, 7.61; N, 11.06; S, 4.22; Cl, 2.80; H20, 1.42. Found: C, 53.94; H, 7.59; N, 10.86; S, 3.93; Cl, 2.70; H₂O, 1.42.

INTERMEDIATES FOR EXAMPLE 1

DNMA—NHCH(OCH₃)CO₂CH₃

DNMA—NHCH(OH)CO₂H (6.0 g, 0.0145 mole) was dissolved in 60 ml MeOH and cooled to 0°. 1.2 ml concentrated H₂SO₄ was added, and the mixture was allowed to warm to 23° overnight. The precipitated solid was filtered, washed with MeOH, Et₂O, and then dried giving the product as a white solid, 3.30 g, 51% yield. The structure was confirmed by NMR and mass spectroscopy. The material was of suitable purity for use in the following step.

DNMA—NHCH(OCH₃)CO₂H

DNMA—NHCH(OCH₃)COOCH₃ (2.41 g, 5.46 mmole) was dissolved in a mixture of 15 ml MeOH and 10 ml 1,4-dioxane. 5.5 ml 1N NaOH was added, and the mixture was stirred for 1 hour and evaporated to an oil under reduced pressure. The oil was suspended in Et₂O and 5.5 ml 1N HCl was added. The phases were separated and the organic phase was washed with saturated NaCl, dried over MgSO₄ and evaporated to a white foam, 2.6 g. The structure was confirmed by NMR and mass spectroscopy. The material was of suitable purity for use in the following step.

INTERMEDIATE FOR EXAMPLE 2

DNMA—NHCH(SCH₃)CO₂H

DNMA—NHCH(OH)CO₂H (6.4 g, 15.4 mmole) was dissolved in 90 ml glacial acetic acid and cooled to 0°. Approximately 6 ml methyl mercaptan was added, followed by 10 ml concentrated H₂SO₄. After stirring for 2 days at 23°, the mixture was poured onto ice and extracted into EtOAc. The organic phase was washed with saturated NaCl and then saturated NaHCO₃ until the pH of the wash was basic. The organic phase, which still contained the product was washed with saturated NaCl, 1N HCl, and saturated NaCl. The organic phase was dried over MgSO₄, and evaporated under reduced pressure to give a white foam, 5.94 g, 89% yield. The structure was confirmed by NMR and mass spectroscopy. The material was of suitable purity for use in the following step.

INTERMEDIATE FOR EXAMPLES 5 AND 6

DNMA—NHCH(SCH(CH₃)₂)CO₂H

DNMA—NHCH(OH)CO₂H (6.4 g, 15.4 mmole) was dissolved in 90 ml glacial acetic acid and cooled to 0°. To the solution was added isopropyl mercaptan (6 ml, 64.6 mmole) and 10 ml concentrated H After stirring for 2 days at 23°, the solution was poured onto ice and extracted into EtOAc. The organic phase was washed with saturated NaCl and then with saturated NaHCO₃ until basic. The organic phase, which still contained the product, was washed with saturated NaCl, 12% HCl, and saturated NaCl. The organic phase was dried over MgSO₄, and evaporated under reduced pressure to a glass, 7.48 g. The structure was confirmed by NMR and mass spectroscopy. The material was of suitable purity for use in the following step.

INTERMEDIATES FOR EXAMPLES 9 AND 10

DNMA—NHCH(OC₂H₅)CO₂C₂H₅

DNMA—NHCH(OH)CO₂H (3.0 g, 7.25 mmole) was dissolved in 100 ml absolute EtOH. Concentrated H₂SO₄ (1 ml) was added, and the mixture was stirred at 23° for 2 days. The mixture was evaporated under reduced pressure to an oil containing suspended solids. The mixture was taken into Et₂O, washed with saturated NaCl and filtered to remove a minor amount of insoluble solids. The organic phase of the filtrate was washed with saturated NaHCO₃ solution, saturated NaCl, 1N citric acid, and saturated NaCl. The solution was dried over MgSO₄ and evaporated to a white foam, 2.94 g. The foam was chromatographed on silica gel, eluting with EtOAc/CHCl₃ (1/1), giving the product as a white foam, 1.39 g, 40.9% yield. The structure was confirmed by NMR and mass spectroscopy. The material was of suitable purity for use in the following step.

DNMA—NHCH(OC₂H₅)CO₂H

DNMA—NHCH(OC₂H₅)CO₂C₂H₅ (1.27 g, 2.70 mmole) was dissolved in 45 ml dioxane. 1N NaOH (5.7 ml) was added, and the mixture was stirred for 1.5 hours. 1N HCl (6 ml) was added and the mixture was evaporated in vacuo to an oily residue.

The oil was taken up into EtOAc and washed with 1N citric acid, saturated NaCl, and dried over MgSO₄. The solution was evaporated to a white foam, 1.37 g. The structure was confirmed by NMR and mass spectroscopy. The product was of suitable purity for use in the following step.

INTERMEDIATE FOR EXAMPLE 11

DNMA—NHCH(NH(CH₂)₃NH₂)CO—S-
TA—NHCH₂CH(CH₃)CH₂CH₃

DNMA—NHCH(SCH₃)CO—S-
TA—NHCH₂CH(CH₃)CH₂CH₃ (3.08 g, 4.6 mmole) was dissolved in 150 ml dry THF and 1,3-diaminopropane (8 ml) was added. HgCl₂ (1 88 g, 6.9 mmole) was added and the suspension was stirred at 23° overnight. The mixture was filtered and the filtrate evaporated to an oil. The oil was dissolved in EtOAc and washed with 12% HCl, saturated NaCl, 1N NaOH and saturated NaCl. The organic phase was dried over MgSO₄ and evaporated under reduced pressure to a white solid, 3.13 g. The structure was confirmed by NMR and mass spectroscopy. The material was used in the following step without further purification.

INTERMEDIATES FOR EXAMPLE 14

DNMA—NHCH(SPh)CO₂H

DNMA—NACH(OH)CO₂H (3.0 g, 7.25 mmole) was dissolved in 90 ml glacial HOAc and cooled to 0°. Thiophenol (1.5 ml, 14.5 mmole) was added, followed by concentrated H₂SO₄ (10 ml). After stirring at 23° for five days, the HOAc was removed under reduced pressure and the residue was suspended in EtOAc. The mixture was washed with saturated NaCl and then with saturated NaHCO₃ until washes were basic. The organic phase, which still contained the product, was washed with saturated NaCl, 1N citric acid, and saturated NaCl. The solution was dried over MgSO₄ and evaporated under reduced pressure to a white foam, 3.97 g. The foam was dissolved in Et₂O and precipitated by addition of hexane giving a gum. The supernatant liquid was decanted, and the residual gum was redissolved in Et₂O. By addition of a small amount of hexane, an orange oil precipitated as an impurity. The solution was decanted from the oil and evaporated under reduced pressure giving the product as white foam, 1.86 g. The structure was confirmed by NMR and mass spectroscopy. The material was used without further purification in the following step.

INTERMEDIATES FOR EXAMPLES 18 AND 19

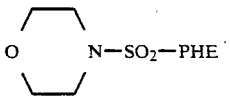

A solution of 66 g (0.4 mole) of PHE in 120 ml of 3.33 N NaOH was treated dropwise over 30 minutes with a solution of 37.1 g (0.2 mole) of morpholinosulfamyl chloride (prepared according to the method of R. Wegler and K. Bodenbennen, Ann. 624, 25 (1959)) in 80 ml of THF. The solution was stirred at room temperature for 6 hours, then acidified to pH 2 with concentrated HCl. The mixture was extracted with EtOAc. The EtOAc phase was washed with 1N HCl, dried over MgSO₄, and evaporated to a solid. Recrystallization from H₂O gave 27 g of the pure product, m.p. 157-158°.

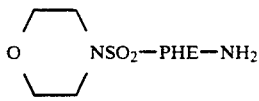

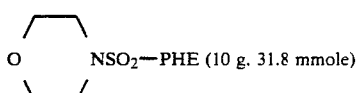

was dissolved in 250 ml CH₂Cl₂/THF (1/1) and cooled to −50°. Carbonyldiimadazole (5.4 g, 33.4 mmole) was added and the mixture was warmed to −15° for 3 hours. The mixture was purged with anhydrous NH₃ gas for 1 hour, followed by warming to 20° for 2 hours. The mixture was evaporated to a gelatinous mass and partitioned between Et$_2$O and H$_2$O. The solid suspended in the Et$_2$O phase was collected and washed with H$_2$O and Et$_2$O. There was obtained 6.0 g of the product as a crystalline solid. The structure was confirmed by NMR and mass spectroscopy. The material was used in the following step without further purification.

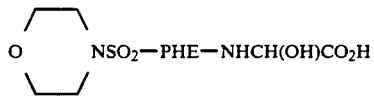

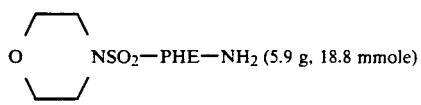

was dissolved in 300 ml of acetone. Glyoxylic acid.H$_2$O (3.64 g, 39.5 mmole) was added and the mixture was heated at reflux for two days. The solvent was removed in vacuo, the residue dissolved in EtOAc, and washed with a minimal amount of saturated NaCl. The organic phase was then washed twice with saturated NaHCO$_3$ solution, the washes combined, and acidified with concentrated HCl to a Congo red end point. The mixture was concentrated in vacuo to a solid, mixed with EtOAc, and filtered. The filtrate was washed with saturated NaCl, dried over MgSO$_4$ and evaporated under reduced pressure to a white foam, 5.27 g. The structure was confirmed by NMR and mass spectroscopy. The material was used in the following step without further purification.

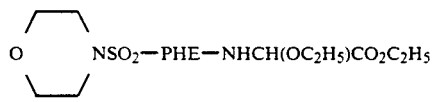

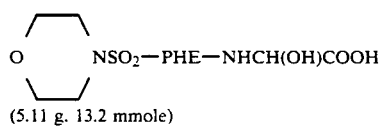

was dissolved in 100 ml absolute EtOH. 1.0 ml concentrated H$_2$SO$_4$ was added, and the mixture stirred at 23° for five days. The mixture was evaporated under reduced pressure to an oil, the oil dissolved in EtOAc, and washed with saturated NaCl, saturated NaHCO$_3$, and saturated NaCl. The EtOAc solution was dried over MgSO$_4$, and evaporated under reduced pressure to a glass, 5.54 g. The material was chromatographed on silica gel, eluting with EtOAc/CHCl$_3$ (1/1), to give 4.22 g of the product as a glass. The structure was confirmed by NMR and mass spectroscopy. The material was used in the following step without further purification.

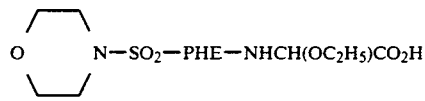

A solution of 4.11 g (9.27 mmole) of

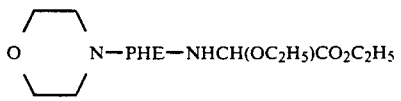

NHCH(OC$_2$H$_5$)CO$_2$C$_2$H$_5$ in 50 ml EtOH was treated with 10 ml of 1N NaOH and stirred for 0.5 hours. An additional 10 ml of 1N NaOH was then added and the stirring continued for an additional 0.5 hours. The mixture was acidified with 13 ml of 1N HCl and the solvent removed under reduced pressure. The residue was taken up in EtOAc, washed with 1N HCl, then saturated NaCl. Drying and removal of the solvent under reduced pressure gave 3.77 g of the product as a white foam. The structure was confirmed by NMR and mass spectroscopy. The material was used in the next step without further purification.

COMMON INTERMEDIATES

DNMA—Cl

Di-(1-naphthylmethyl)acetic acid (46.8 g, 0.137 mole) was dissolved with warming to 30° in 120 ml thionyl chloride. After stirring overnight, the solvent was removed under reduced pressure until the residual oil began to crystallize. 400 ml Et$_2$O was then added, giving a suspension, to which was added 500 ml hexane. The mixture was concentrated under reduced pressure, cooled and filtered. The solid was washed with hexane and dried giving the product as a white solid, 2.94 g. The structure was confirmed by NMR and mass spectroscopy. The material was of suitable purity for use in the following reaction.

DNMA—NH$_2$ 150 ml THF was cooled to −60° and saturated with anhydrous NH$_3$ gas. While continuing the NH$_3$ purge, a solution of DNMA—Cl (16.0 g, 0.045 mole) in 125 ml THF was added over 15 minutes. A solid formed, and the NH$_3$ purge was discontinued. After warming to 23° overnight, the mixture was stripped to a solid and taken up in 350 ml EtOAc. The EtOAc was washed with 1N citric acid, saturated NaCl solution, saturated NaHCO$_3$ solution, and saturated NaCl solution. The organic phase was dried over MgSO$_4$ and stripped under reduced pressure to a solid. The solid was recrystallized from EtOAc/Et$_2$O, filtered, and dried, giving the product as a white solid, 13.4 g, 88% yield. The structure was confirmed by NMR and mass spectroscopy. The material was of sufficient purity for use in the following step.

DNMA—NHCH(OH)CO$_2$H

DNMA—NH$_2$ (12.9 g, 0.038 mole) and glyoxylic acid hydrate (4.34 g, 0.047 mole) were dissolved in 250 ml acetone and heated to reflux for 18 hours. The mixture was evaporated to an oil, the oil dissolved in Et$_2$O and washed with saturated NaCl. Upon washing with saturated NaHCO$_3$, a solid precipitated which was filtered, triturated with EtOAc and resuspended in EtOAc. An equal volume of water was added, and pH was adjusted to a Congo red end point by the addition of citric acid. Solution occurred and the phases were separated. The organic phase was washed with saturated NaCl, dried over MgSO₄, and evaporated to a foam, 12.7 g, 80% yield. The structure was confirmed by NMR and mass spectroscopy. The material was of suitable purity for use in the following step.

BOC—STA—NHCH₂CH(CH₃)CH₂CH₃

BOC—STA (27.53 g, 0.1 mole, U.S. Pat. No. 4,397,786) and HOBT.H₂O (14.2 g, 0.105 mole) were dissolved in 40 ml DMF. 300 ml CH₂Cl₂ was added, and the mixture was cooled to 0°. A solution of DCC (21.66 g, 0.105 mole) in 50 ml CH₂Cl₂ was added, followed by S-2-methylbutylamine (12 ml, 0.1 mole). After stirring at 0° for 2 hours, the mixture was allowed to warm to 25° over 1.5 hours. The mixture was filtered, and the solvent was removed in vacuo. The residue was dissolved in EtOAc, which was washed with 1N citric acid, brine, saturated NaHCO₃ solution, and brine. The organic phase was dried over MgSO₄, filtered, and stripped to a gum, 36.90 g. The gum was dissolved in Et₂O and treated with charcoal to remove colored impurities. The suspension was filtered and stripped to a gum, 35.2 g, which was suitable for use in the following procedure without further purification.

STA—NHCH₂CH(CH₃)CH₂CH₃

A solution of 38.0 g, (0.11 mole) of BOC—S-TA—NHCH₂CH(CH₃)CH₂CH₃ in 250 ml CH₂Cl₂ was treated with HCl gas every one-half hour over a 3 hour period. The solvent was removed under reduced pressure and the residue taken up in 30 ml H₂O and 110 ml of 1N HCl. The solution was washed twice with Et₂O, the pH brought to 13 with 1N NaOH, and the solution extracted twice with Et₂O. The Et₂O was washed with saturated NaCl, dried, and the solvent removed under reduced pressure giving 22.3 g of the product as an oil which solidified on standing. The material was sufficiently pure for use in subsequent reactions.

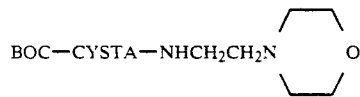

A solution of 17.7 g (0.056 mole) of BOC-STA and 7.59 g (0.056 mole) of HOBT in 250 ml of DMF was cooled in ice and treated with a solution of 11.7 g (0.056 mole) of DCC in 20 ml of DMF. After stirring for 5 minutes, the solution was treated with 7.6 ml (0.056 mole) of 4-(2-aminoethyl)morpholine. The solution was stirred for 0.5 hours at 0°, then at room temperature overnight. The dicyclohexylurea was filtered off and the solvent removed under high vacuum. The residue was taken up in EtOAc, washed with saturated NaHCO₃, H₂O, then saturated NaCl, and then dried over MgSO₄. Removal of the solvent under reduced pressure gave the crude product which was purified by chromatography on silica gel, eluting with CHCl₃/MeOH (95/5). There was obtained 24 g of pure product.

Similarly, substituting BOC-CHSTA (DE-3,610,593), BOC-ACYS(Z) (EP-198,271), BOC-DFKCYS (EP-222,523), or BOC-DFKSTA (GB-2,171,103) for BOC-CYSTA in the above preparation gives the corresponding amides,

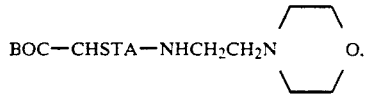

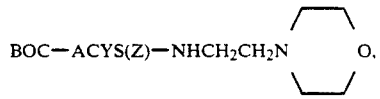

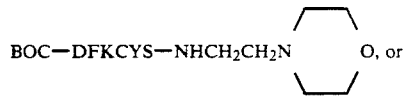

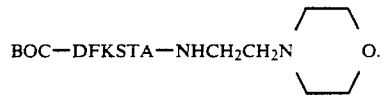

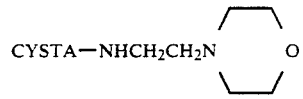

A solution of 24 g (0.056 mole) of

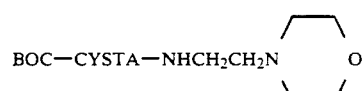

in 300 ml of CH₂Cl₂ was treated with HCl gas for 5 minutes. A gum formed which was redissolved by the addition of 100 ml of MeOH. HCl gas was bubbled in for an additional 10 minutes, and the solution allowed to stir at room temperature for 3 hours. The solvent was removed under reduced pressure and the residue taken up in CH₂Cl₂. This was treated with CH₂Cl₂ that had been saturated with NH₃ gas at 0°. The NH₄Cl was filtered off and the filtrated evaporated. There was obtained 15.2 g of an oil which solidified on standing. The structure was confirmed by NMR spectroscopy.

Substitution of

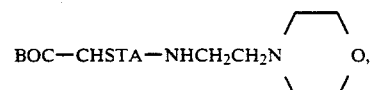

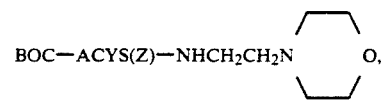

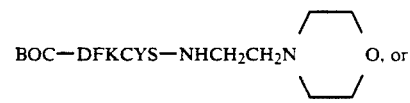

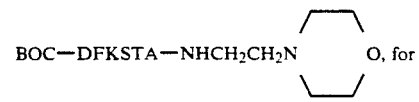

-continued

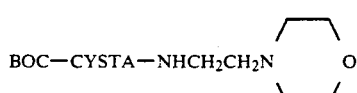
BOC—CYSTA—NHCH₂CH₂N   O in the above preparation gives the corresponding deviatives.

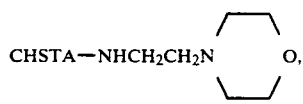
CHSTA—NHCH₂CH₂N   O,

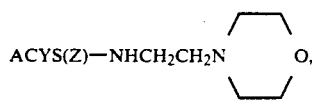
ACYS(Z)—NHCH₂CH₂N   O,

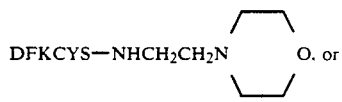
DFKCYS—NHCH₂CH₂N   O, or

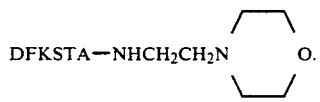
DFKSTA—NHCH₂CH₂N   O.

These may be converted to certain peptides of the present invention by following the procedures outlined in Examples 18 and 19. In the case of the

ACYS(Z)—NHCH₂CH₂N   O derivative, a final removal of the Z-group from the precursor peptide gives certain other peptides of the present invention.

We claim:

1. A compound selected from the group consisting of:

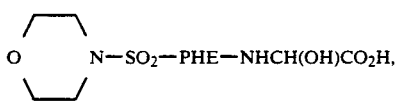
O   N—SO₂—PHE—NHCH(OH)CO₂H,

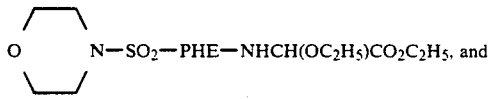
O   N—SO₂—PHE—NHCH(OC₂H₅)CO₂C₂H₅, and

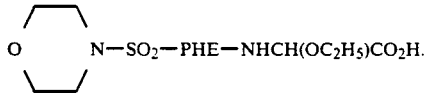
O   N—SO₂—PHE—NHCH(OC₂H₅)CO₂H.

* * * * *